(12) United States Patent
Frydman

(10) Patent No.: US 6,873,153 B2
(45) Date of Patent: Mar. 29, 2005

(54) METHOD AND APPARATUS FOR ACQUIRING MULTIDIMENSIONAL SPECTRA AND IMPROVED UNIDIMENSIONAL SPECTRA WITHIN A SINGLE SCAN

(75) Inventor: Lucio Frydman, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 10/728,069

(22) Filed: Dec. 4, 2003

(65) Prior Publication Data

US 2005/0007111 A1 Jan. 13, 2005

Related U.S. Application Data

(63) Continuation-in-part of application No. PCT/US03/21314, filed on Jul. 7, 2003.

(51) Int. Cl.[7] .................................................. G01V 3/00
(52) U.S. Cl. ...................................... 324/307; 324/309
(58) Field of Search ................................ 324/307, 309, 324/311, 318, 300; 600/470

(56) References Cited

U.S. PATENT DOCUMENTS 5,572,125 A * 11/1996 Dunkel ........................ 324/307
5,813,987 A * 9/1998 Modell et al. ............... 600/473

* cited by examiner

Primary Examiner—Brij B. Shrivastav
(74) Attorney, Agent, or Firm—Martin Fleit; Paul D. Bianco; Fleit Kain Gibbons Gutman Bongini & Bianco P.L.

(57) ABSTRACT

Method and apparatus for treating a sample to acquire multidimensional spectra within a single scan that partitions a sample into a set of independent subensembles endowed with different resonance frequencies. A polychromatic irradiation of the sample is implemented whereby the various subensembles are selectively manipulated by a time-incremented series of excitation or refocusing sequences. Thereafter, a homogeneous sequence capable of generating an observable spectral signal from each of the subensembles is applied with simultaneous monitoring of the observable signals arising from the various subensembles in a resolved fashion the observable signals acquired in this manner are processed into a complete multidimensional spectral data set.

60 Claims, 22 Drawing Sheets

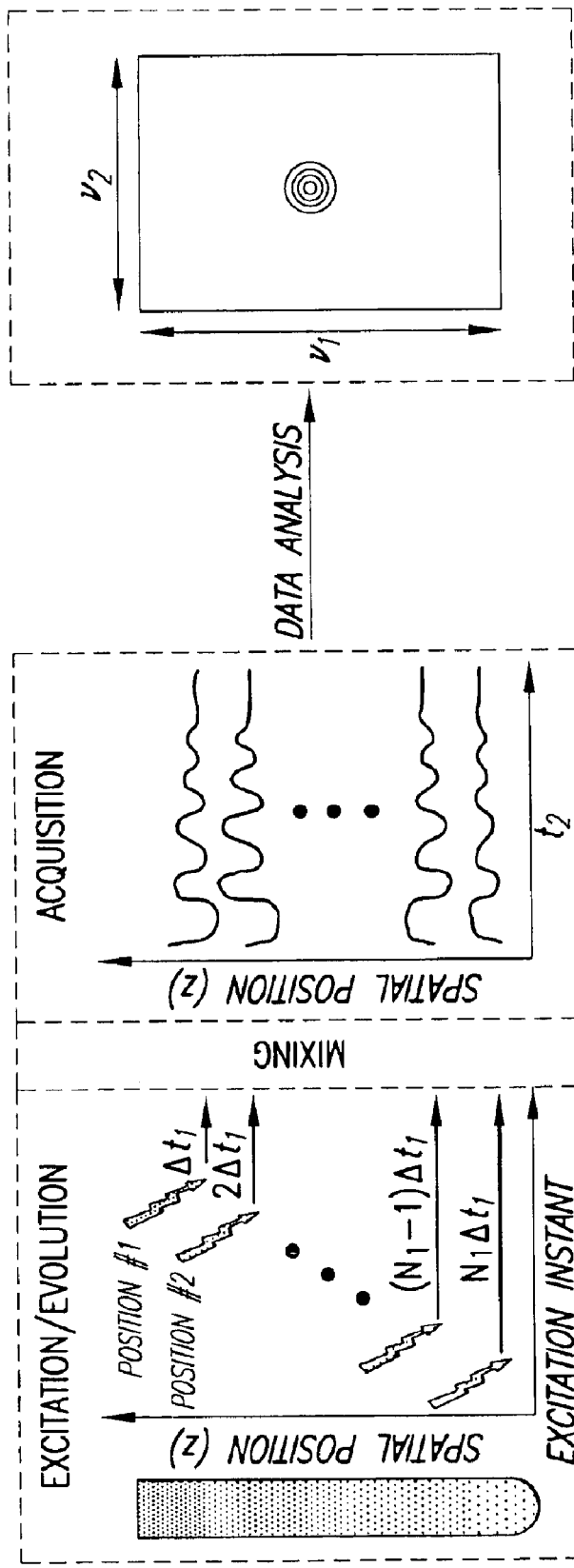

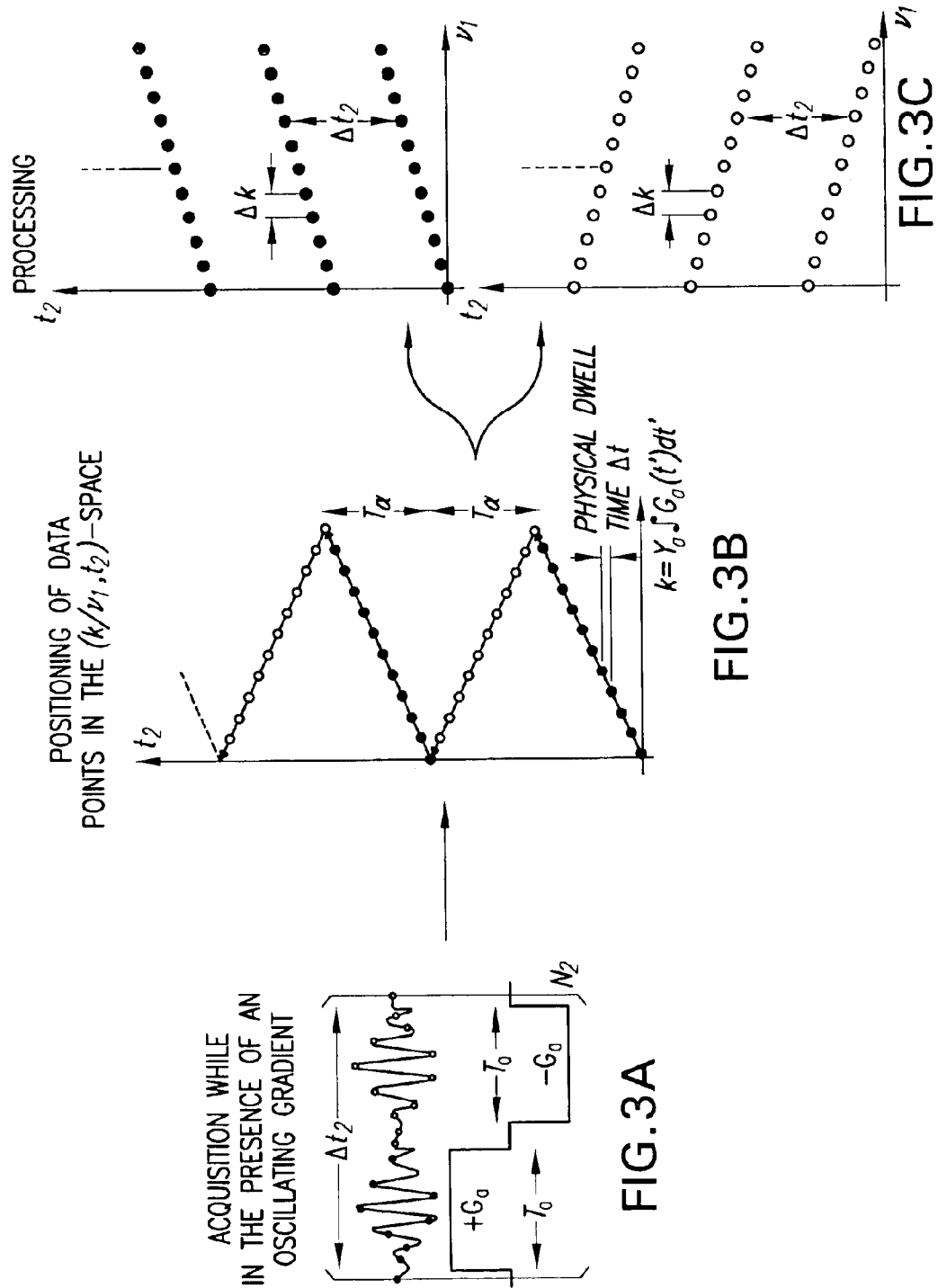

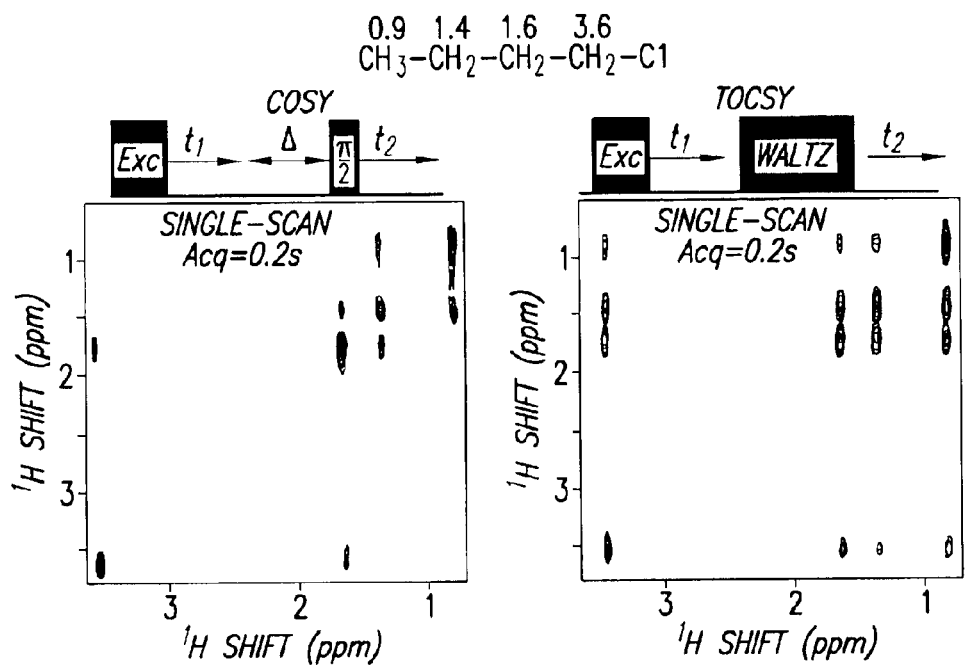
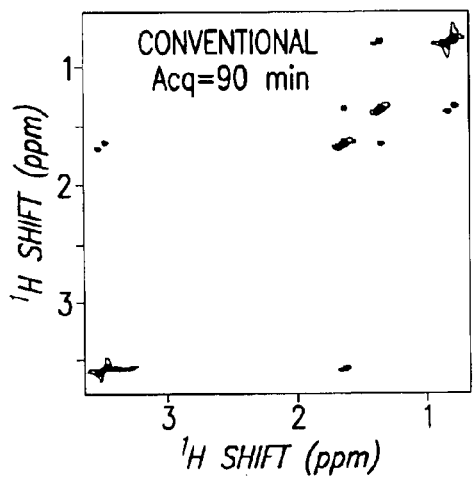
FIG.6C
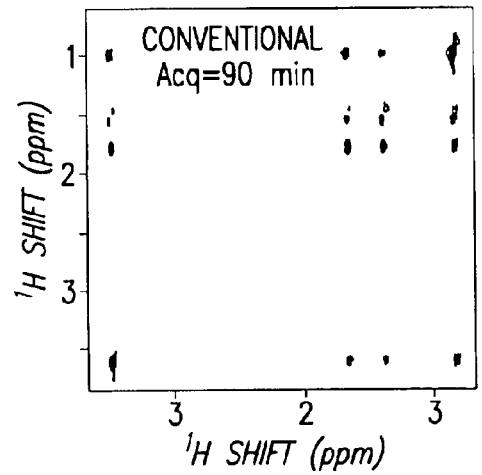
FIG.6D

SINGLE-SCAN 2D IMAGE

SINGLE-SCAN 2D IMAGE $H_2O$ PHANTOM IMAGED $H_2O$-FILLED TUBE

CAPILLARY GLASS ROD $r_1 = 18mm$ $r_2 = 5mm$

METHOD AND APPARATUS FOR ACQUIRING MULTIDIMENSIONAL SPECTRA AND IMPROVED UNIDIMENSIONAL SPECTRA WITHIN A SINGLE SCAN

RELATED APPLICATION

This application is a continuation-in-part of PCT/US03/21314 filed Jul. 7, 2003, the contents of which are here incorporated in their entirety.

BACKGROUND OF THE INVENTION

1. Field of the Invention

The present invention relates to a new method and apparatus for acquiring uni-dimensional and multi-dimensional spectra within a single scan, and more particularly, to a method and apparatus for acquiring uni- and multi-dimensional nuclear magnetic resonance spectra within a single scan. The present invention also relates to a variety of methods employing the principles of these methods or techniques.

2. State of the Art

In terms of applicability to unravel the nature of molecular systems, few analytical techniques rival the insight furnished by spectroscopy studies based on the acquisition of multidimensional spectra. Such spectroscopies include optical, paramagnetic, electron, mass and nuclear magnetic resonance (NMR) spectroscopies. Included among this latter category is the method known as magnetic resonance imaging (MRI). Whether used to discover new pharmaceutical drugs, to characterize new catalysts, to investigate the structure and dynamics of proteins, or to carry out a non-invasive imaging diagnosis, few analyses are nowadays performed without the aid of at least some form of multidimensional experiment, and especially a multidimensional NMR experiment. One drawback of these protocols is that, by contrast to one-dimensional spectroscopic methods, multidimensional techniques, and particularly multidimensional NMR, requires relatively long measurement times associated with the acquisition of hundreds or thousands of scans. This places certain kinds of rapidly changing systems in Chemistry, such as proteins changing conformation, analytes flowing through a chromatography column, unstable biomolecules, outside their realm. Also unsuitable to relatively slow multidimensional NMR analyses are the thousands of compounds that can currently be made available by a single combinatorial-chemistry assay. Long acquisition times also make multidimensional NMR, as presently performed, ill-suited for in vivo analyses, and for clinical measurements in combination with spatial localization techniques.

SUMMARY OF THE INVENTION

Accordingly, the object of the present invention is to provide a method and apparatus for acquiring multidimensional spectra, and especially multidimensional nuclear magnetic resonance spectra, within a single scan. This is accomplished by a novel method and apparatus that enables treating a sample to acquire multidimensional spectra within a single scan comprising the steps of: (1) partitioning, at least notionally, a sample into a set of independent subensembles endowed with different resonance frequencies; (2) implementing a polychromatic irradiation of the sample whereby the various subensembles are selectively manipulated by a time-incremented series of excitation or refocusing sequences; (3) follow these various selective manipulation processes by a homogeneous sequence capable of generating an observable spectral signal from each of the subensembles; (4) simultaneously monitoring the observable signals arising from the various subensembles in a resolved fashion; and (5) processing the set of signals acquiring in this manner into a complete multidimensional spectral data set. The acquisition of the multidimensional spectra can result from the practice of any type of spectroscopy.

In a further development of the present invention, the object of the present invention is to provide a method and apparatus for acquiring multidimensional spectra, and especially multidimensional nuclear magnetic resonance spectra, within a single scan. For the case of NMR, this is accomplished by a novel method and apparatus that enables the acquisition of multidimensional NMR spectra within a single continuous scan. Provided that an analyte's signal is sufficiently strong, the invention can, in turn, shorten the acquisition time of any multidimensional application or experiment by several orders of magnitude. The new invention is compatible with the majority of multidimensional NMR pulse sequences hitherto proposed, and can be implemented using known magnetic resonance hardware. The same single-scan protocol providing the spectroscopic information can additionally be exploited to extract information about the spatial location of the analyte's originating the signal. Spatially resolved MRI information can thus be extracted from the protocol at no additional experimental costs and/or penalties.

Additional derivations arise from the partitioning of the sample exploited by this invention to collect NMR spectra, that relate not only to multidimensional acquisitions but also to the ways in which unidimensional NMR data is collected. One of the opportunities enabled by this invention is the use of indirect schemes to detect in a single scan the NMR spectra of insensitive nuclei Iby monitoring instead the NMR signal arising from neighboring nuclei S of higher sensitivity. Another one resides in the feasibility of collecting high resolution NMR spectra even upon using inhomogeneous or unstable magnetic fields, by manipulating the phases used to excite and detect the signals arising from each of the excited slices.

Accordingly, the foregoing objectives are accomplished by a method and apparatus for treating a sample to acquire multidimensional magnetic resonance spectra within a single scan (or a small number of scans) comprising the steps of: (1) applying a magnetic field gradient on the sample so as to endow spins at different positions within the sample with different resonance frequencies; (2) applying a train of frequency-incremented radiofrequency (RF) pulses in unison with this gradient (or with an oscillating version of thereof), so as to endow spins at different positions within the sample with incremented values of their evolution times, thus creating an effective spatial encoding of the spins' frequencies (3) applying if needed a homogeneous mixing pulse sequence at the conclusion of the various spatial encoding processes, capable of creating a set of observable spin signals; (4) capturing the signals thus created from the sample while decoding the spins' spatial locations using a second set of acquisition magnetic field gradient; (5) subjecting the collected data to a suitable rearrangement and Fourier analysis procedure so as to retrieve the final spectrum being sought.

Lying at the core of this new invention is the application of a magnetic field gradient, operated in unison with a train of spatially-selective radiofrequency (RF) pulses. This enables the invention in a first step to endow spins at different positions within the sample with incremented values of their indirect evolution times, leading to an encoding of the internal evolution frequencies of spin coherences along a spatial coordinate. This indirect-domain information is preserved throughout a mixing process step, and subsequently decoded in a step that utilizes an acquisition gradient applied while the signal from the spins is being captured in a recording step. The application of a proper acquisition gradient can successfully decode the information that was encoded during the course of the initial evolution time, in the form of an observable echo signal. The timing of this echo will depend on the strength of the $\Omega_1$ internal interaction that acted on the spins prior to the mixing step, hence allowing, mapping of the spectrum along the indirect domain. Furthermore, this unwinding step can be immediately reversed, and then, repeated multiple ($N_2$) times by alternating the sign of the acquisition gradient, thereby allowing monitoring of the $\Omega_2$ frequencies of the spins active during the second, directly-detected $t_2$ period. Signals obtained during such cyclic rephasing/dephasing train can be arranged into a bidimensional data set, which by Fourier analysis along $t_2$ will lead to a desired 2D NMR spectrum correlating ($\Omega_1$ and $\Omega_2$ frequencies. The incorporation of multiple linearly-independent gradient geometries also enables an extension of this protocol to arbitrary N-dimensional NMR processing or experiments, where frequencies along N−1 indirect domains are spatially encoded using the new method and the final time-domain is monitored in the usual direct fashion. Fourier analysis of the spectral peaks along the indirect $k/v_1$ dimension provide as a fringe benefit the spatial positioning of the associated metabolite, thus yielding MRI information within the same experimental set.

There are many applications and uses of the present invention. To render a more comprehensible understanding of the invention, the following description will be with particular reference to NMR. However, it should be clearly understood that the applicability of the invention is to any type of spectroscopy as enumerated in the foregoing. The ensuing discussion will be limited primarily to NMR for the sake of simplification and not by way of any limitation of the scope of the teachings herein.

Recent developments in probehead and magnet technologies have increased NMR's sensitivity by almost an order of magnitude during the last decade, see R. F. Service, *Science* 279, 1127 (1998) and A. Constans, *The Scientist* 17, 45 (2003), thus limiting the acquisition times of many multidimensional NMR experiments to signal digitization rather than to signal-to-noise (S/N) considerations. There are several areas where this bonus in signal enhancement is combinable with significant reductions in acquisition times brought about by the new method and apparatus of the invention, to speed up existing investigations or make new kinds of hitherto unfeasible investigations possible. The subordinate methods of the present invention include i. The novel method of the analysis by multidimensional NMR of rapidly-changing dynamic systems. The possibility of completing the collection of multidimensional NMR spectra within a 0.1 sec time scale will, enable our invention to monitor in real time, a variety of chemical and physical processes and reactions that are hitherto outside the capabilities of NMR. These include the real-time monitoring of ongoing chemical reactions, and the folding of biological macromolecules.

ii. The novel method for the application of multidimensional NMR to hyperpolarized spin states. A number of methods have been developed to enable the generation of very highly polarized spin states. These systems can impart on atoms and molecules NMR signals that are ca. five orders of magnitude more intense than a conventional NMR signal, but they are transient states that decay relatively rapidly and take long times to be generated. Only single-scan experiments are thus usually implemented on such hyperpolarized spin systems. The present invention enables the routine application of complex multidimensional NMR experiments to such hyperpolarized systems, enabling extensions of chemical studies.

iii. The novel method for the characterization of analytes subject to flow through a NMR spectrometer, and thereby the coupling of multidimensional NMR with high-throughput chromatographic techniques. The combination of NMR with chromatographic techniques opens one of the most promising routes to the characterization of chemical and biochemical samples. The residence time of such flowing samples through the NMR reception coil, however, is very limited ($\approx$1 sec). Therefore only unidimensional NMR spectra have been so far collected in real time on this kind of samples. The method of the present invention will enable the acquisition of multidimensional NMR spectra on samples being chromatographed, thereby providing a new and much more powerful way to characterize plant extracts, natural products, amino acids, peptides, nucleic acids and other types of chemicals being separated in a chromatographic column.

iv. The novel method for rapid survey of large numbers of chemicals, like those made nowadays available by Combinatorial Chemistry. Combinatorial Chemistry is a novel approach to the synthesis of organic, inorganic and pharmacological molecules, whereby thousands of compounds are synthesized and tested in a variety of ways for chemical and/or biological activity. Combinatorial methods have provided much of the impetus for the ongoing revolution currently undergoing in Proteomics and Metabonomics. The enormous number of compounds that this approach requires be tested only allows high-throughput analytical techniques to participate in these tests and characterizations. The invention described herein allows the incorporation of ultrafast multidimensional NMR methods to this array of high-throughput techniques, thereby providing a new route to the discovery of new catalysts, new pharmaceuticals, pharmaceutically-active peptides and nucleic acids, etc.

v. The novel method for the acceleration of quantum computing algorithms. NMR offers one of the most practical approaches to implement a quantum computer. The present invention enables the speeding up of such multidimensional NMR quantum computers by several orders of magnitude.

vi. The novel method for the structural elucidations of large molecules, and in particular of systems involving proteins and nucleic acids. NMR-based structural elucidations on high molecular weight, complex systems will eventually demand the use of a large number of spectral dimensions (over 4) for achieving sufficient spectral resolution of the peaks. At the same time, however, large molecules in general and biological macromolecules under physiological conditions in particular, are usually incapable of withstanding the long acquisition times hitherto associated with such experiments. By speeding the times required to implement such experiments by several orders of magnitude the present invention bypasses such limitation, providing a new way to obtain the structure of macromolecules in their native states.

vii. The novel method of the present invention for conducting in vivo spectroscopy and the following of fast metabolic processes using ultrafast multidimensional NMR. Indeed, multidimensional NMR spectroscopy on animals and/or humans is currently hampered by the long times that subjects need to reside within the NMR magnet for the completion of the experiments, a demand which should be greatly eased by the practice of this novel invention. This will enable a new route to the clinical diagnosis of disease whether as a pure spectroscopic tool or in combination with methods for spatial localization.

viii. The novel method for conducting MRI protocols, relying on magnetic field gradients to both speed up the acquisition of the spectral data as well as for locating the spatial position of spins in a non-invasive fashion. This opens new routes for the accelerated acquisition of clinical diagnostic and research MR images. The new ultrafast multidimensional MRI method of the present invention that results can be employed to monitor brain metabolism, pulsating regions (thorax, abdomen), etc. It can also aid for the real-time positioning of malignancies and hence as aid in surgical procedures.

ix. The novel method to extract from multidimensional spectra collected within a single continuous scan, information about the spatial localization of the sample using a post-processing of the collected data. Multidimensional spatial localization can thus be combined with multidimensional spectral information within the same short time scale. This will enable a new approach to clinical diagnosis and basic physiological research.

x. The novel method to shorten by orders of magnitude the duration of unidimensional NMR spectra collected for low-γ nuclei, by monitoring their shape indirectly via their more sensitive neighbors. For instance when dealing with heteronuclear $^{15}$N NMR studies of organic molecules, the sensitivity of single-scan experiments based on using the invention for monitoring their 1D NMR spectra via the signals of neighboring $^1$H nuclei could increase by ca. 5–10. This should greatly facilitate the research of medicinal chemists, utilizing heteronuclear NMR as a main tool for the preparation and characterization of pharmacologically-active and natural products.

xi. The novel method to enable the acquisition of high resolution NMR spectra even when dealing with inhomogeneous or unstable magnetic fields. A considerable cost of current NMR and MRI instrumentation, stems from the need of building intense magnets possessing homogeneities in the order of 1 part-per-million (ppm) over the specimen volume. Only thus can high-resolution NMR spectra be resolved. Furthermore these magnetic fields need to remain unchanged ("locked") over the course of the whole spectral data acquisition, least their change ends up broadening the spectral response from the spins. By departing from the usual way of encoding and collecting NMR data the invention can alleviate both of these demands. High resolution spectra even when dealing with inhomogeneities that are orders-of-magnitude larger than those currently tolerable. This can have important consequences in the hardware used to collect uni- and multi-dimensional NMR spectra: much less sophisticated "tabletop" magnets could become routine for analytical use in high resolution NMR characterizations, and electromagnets whose stability and homogeneity are currently too poor (including the extremely high field Bitter magnets) could become suitable for the much higher demands of NMR and MRI xii. The novel method for extending single-scan multidimensional spectroscopy to techniques other than NMR, such as, mass spectrometry, electron paramagnetic resonance, as well as a variety of pulsed infrared, optical and UV spectroscopies. As in the case of NMR, these techniques are based on monitoring the response of the system as a function of an incremented time variable, thereby requiring the collection and processing of numerous individual scans. By adapting the ideas of a reversible inhomogeneous frequency broadening coupled to the selective excitation of sub-ensembles within the sample, the novel method of the present invention enables other kinds of multidimensional spectroscopies to be reduced to a single-scan acquisition.

Other and further objects and advantages of the present invention will become more readily apparent from the following detailed description of preferred embodiments of the invention when taken in conjunction with the appended drawings.

BRIEF DESCRIPTION OF THE DRAWINGS

FIGS. 1A–B present graphically and pictorially steps of the invention as they relate to the underlying the acquisition of 2D NMR spectra within a single scan.

FIGS. 3A–C present graphically and pictorially the steps of the invention as they relate to the acquisition while in the presence of an oscillating gradient; positioning of data points in the $(k/v_1, t_2)$-space; and further repositioning of the collected data points in preparation for a fast Fourier transform processing.

FIGS. 6A–D compare graphically and pictorially the similar results afforded by conventional vis-à-vis ultrafast 2D $^1$H-$^1$H COSY and TOCSY NMR on a chemical sample.

DETAILED DESCRIPTION OF PREFERRED EMBODIMENTS OF THE INVENTION

Figure 2A:
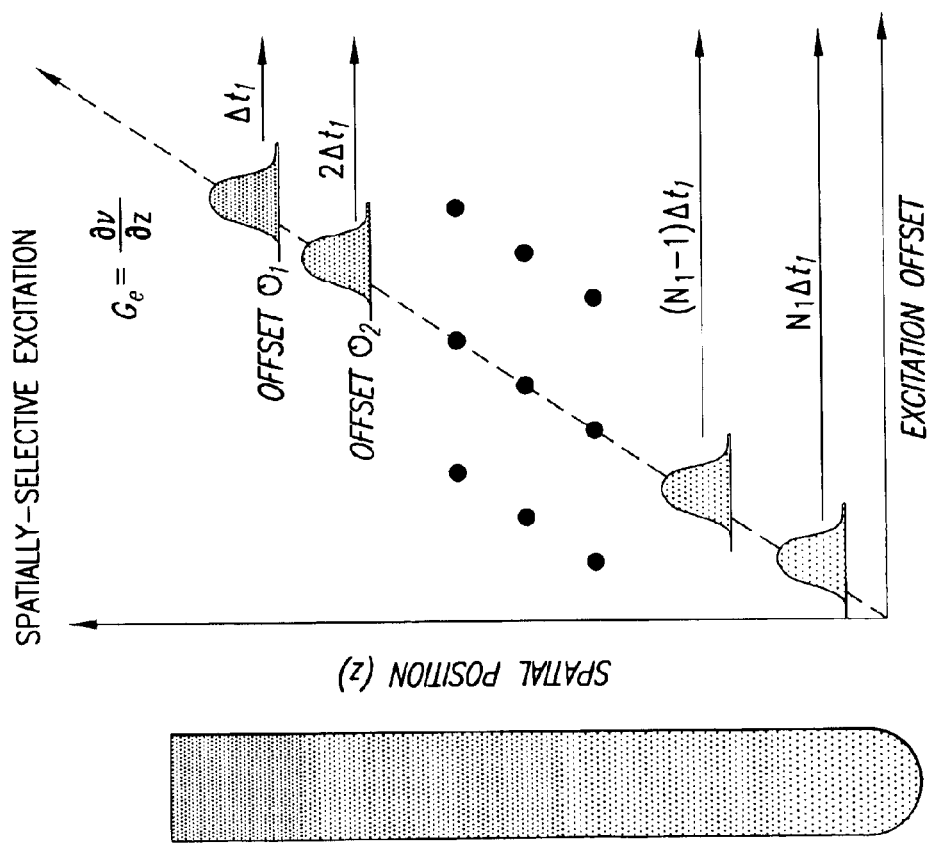
FIGS. 2A–B present graphically and pictorially the steps of the invention as they relate to carrying out the selective excitation step in the initial stage of FIG. 1, without encoding excitation artifacts, by means of a gradient-echo refocusing.

Referring now to the drawings, preferred embodiments of the present invention will be described in detail.

The paradigm for 2D NMR as laid down by the core contributions of Jeener and Ernst, see J. Jeener, in *Ampere International Summer School II*, Basko Polje, Yugoslavia (1971) and W. P. Aue, E. Bartholdi and R. R. Ernst, J. Chem. Phys. 64, 2229 (1976), is summarized by the well-known scheme $$\text{Preparation/Excitation–Evolution } (t_1)\text{–Mixing–Detection } (t_2) \quad (1)$$

However, according to the present invention, a 2D spectrum $I(v_1, v_2)$ can be obtained if this approach is followed to collect a two-dimensional signal S as a function of $t_1$ and $t_2$, and subsequently Fourier transformed. Yet the signals that are actually generated by the nuclear spin ensemble can only be directly detected as a function of $t_2$, and hence the spins' coherent evolution as a function of the remaining time variable cannot be monitored directly. According to the invention, the remaining time variable is monitored indirectly in a unique manner. Independent acquisitions are thus carried out where the value of $t_1$ is systematically incremented; since the mixing process step occurring prior to $t_2$ preserves the encoding imparted during the $t_1$ evolution, Fourier transformation (FT) of the digitized signals as a function of the $t_1$ parameter reveals the nature of the $\Omega_1$ frequencies that affected spins prior to the mixing.

It is clear that this 2D NMR scheme, involving homogeneous and sequential evolution, mixing and acquisition periods for all spins throughout the sample, is not amenable to implementation within a single scan. The ultrafast 2D NMR methodology that is proposed by the present invention bypasses this limitation by partitioning the sample into a series of independent subensembles, each of them characterized by an individual $t_1$ evolution. Such partitioning can be done, for instance, by applying a time-incremented series of $N_1$ selective excitation sequences throughout an inhomogeneously-broadened sample (FIG. 1). A homogeneous mixing period (FIG. 1A) followed by the observation of the independent signals generated by each member of this set, can then enable the simultaneous acquisition of a complete conventional-type 2D NMR data set (FIG. 1B). The overall acquisition scheme would then be summarized as $$\left[\begin{array}{c}\text{Selective}\\\text{Preparation/Excitation}\end{array}\right]_{N_1} - \underset{\text{Evolution}(t_1)}{\text{Inhomogeneous}} - \underset{\text{Mixing}}{\text{Homogeneous}} - \underset{\text{Acquisition}(t_2)}{\text{Inhomogeneous}} \quad (2)$$

Though evidently more complex than the original 2D NMR scheme in eq. (1), this partitioning of the sample offers the potential to collect the complete bidimensional data set within a single scan. This of course, depends on techniques for endowing the various $N_1$ sub-ensembles with individual $t_1$ evolution times, and then for monitoring the signals that these generate independently and within a single transient.

FIGS. 1A and 1B show graphically and pictorially the method of the present invention and more particularly, depict a simplified scheme or method respecting the application of spatially-heterogeneous excitation and detection schemes, toward the acquisition of multidimensional NMR data within a single scan. The excitation that triggers the initial spin evolution is assumed to affect spins in different positions within the sample at a series of incremented times (FIG. 1A). This creates a spatial encoding of the initial $t_1$ evolution period, which is then monitored as a function of $t_2$ via the spatially-resolved acquisition of the NMR signal. Following a suitable processing of the signals monitored as a function of the $t_2$ and spatial variables, this strategy allows one to retrieve a complete 2D NMR spectrum within a single scan (FIG. 1B).

It is possible to propose several alternatives for achieving the spatially heterogeneous evolution and detection processes described in eq. (2) and FIG. 1. Out of the possible alternatives, the invention concentrates for simplicity on those illustrated in FIGS. 2A and 2B for the excitation process, and in FIGS. 3A, 3B and 3C for the acquisition stage. FIG. 2A shows that a train of frequency-shifted RF excitation pulses possessing different offsets $O_i$ can be applied while in the presence of a magnetic field gradient, in order to achieve the incremented evolution ($t_1$) of spins throughout the sample assumed by the protocol in FIG. 1A. The train of frequency-shifted pulses needs to be applied in combination with a synchronized reversal in the sign of the field gradient (gradient echoes) if an evolution that is solely dictated by the internal spin evolution frequencies is to be achieved. Assuming that gradients in this pair are applied for equal time lengths $T_p$ (e.g., the RF pulse duration), this will result in a gradient echo where any dephasing that may have affected hitherto excited magnetizations becomes compensated.

FIGS. 3A, 3B and 3C illustrate the protocol employed in order to achieve the spatially-resolved data acquisition stage that is required by the method or scheme as given in FIG. 1A. Dots symbolize the data points digitized during the course of positive and negative acquisition gradients. This oscillatory gradient module is then repeated $N_2$ times, with $N_2$ defining the number of effective points along $t_2$. In FIG. 3B data points monitored during the hybrid spectroscopic-imaging module defined in FIG. 1A need then to be separated according to their respective k and $t_2$ variables, with $k = \int_0^{t_2} \gamma_a G_a(t) dt$. The open and closed dots symbolize the coordinates of such points. In FIG. 3C, as data stemming from the rearrangement illustrated in FIG. 3B are not arrayed within a regular grid ready to be processed using the fast FT algorithm, points are sorted once again into two independent bidimensional data sets that are then ready to be individually processed. Both 2D data sets can then be co-added after their processing for the sake of improving the overall S/N of the method or experiment.

Figure 2B:
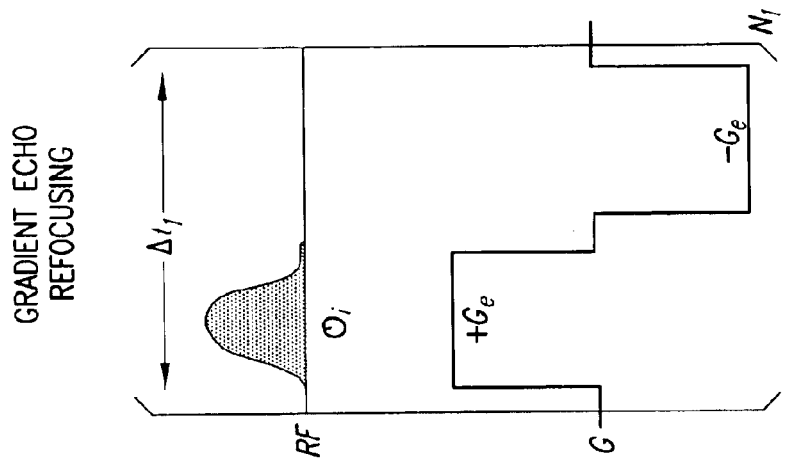

According to the invention, when dealing with a conventional isotropic sample, the simplest route to achieve an inhomogeneous set of evolution times is by imposing an auxiliary gradient on top of the homogeneous external magnetic field $B_O$. This in turn enables a sequential excitation of the spins, based on the use of a train of frequency-shifted selective RF pulses (FIG. 2A). Using a gradient-based step or scheme requires imparting on successively-excited spin packets an evolution phase that reflects solely the internal coupling frequencies, but not the frequencies defined by the artificial gradient. This step or goal is achieved by the invention by following the action of each selective pulse with reversal of the $+G_e$ gradient employed to implement the spatially-heterogeneous excitation via an opposite gradient of amplitude $-G_e$ (FIG. 2B). Assuming that gradients in this pair are applied for equal time lengths $T_p$ (e.g., the RF pulse duration), this will result in a gradient echo where any dephasing that may have affected hitherto excited magnetizations becomes compensated. Alternatively a continuous, frequency-swept (chirped) excitation may be used to achieve a similar goal of a encoding along a spatial dimension the time incrementation of the spins.

The next aim is to monitor the signals originating from these individually-excited slices, after they have been subject to the mixing process step. This spatially-resolved detection of the signal as a function of $t_2$ amounts to a hybrid spectroscopic/imaging experiment, an acquisition that can be implemented within a single scan using a number of alternatives, see for example, P. T. Callaghan, "Principles of Nuclear Magnetic Resonance Microscopy" Oxford University Press, Oxford, 1991, and B. Blumich, "NMR Imaging of Materials" Oxford University Press, Oxford, 2000. In particular, during this stage of the methodology's development, the collection of NMR signals while subject to an alternating field gradient (see FIGS. 3A, 3B and 3C) was adopted towards this end, see for example P. Mansfield, *Magn. Reson. Med.* 1, 370 (1984). This leads to signals becoming simultaneously encoded according to the spins' spatial positions, as well as, according to their internal evolution frequencies. Such encoding can be summarized by an evolution phase $\phi=k\cdot z+t_2\cdot \nu_2$, where $$k = \int_0^{t_2} \gamma_a G_a(t)\, dt$$

is a gradient-related wave number encoding position, and $t_2$ reflects the extent of the free evolution and encodes the internal frequency. Evolution while in the presence of an oscillating $\pm G_a$ gradient can then be represented by a "zig-zagging" trajectory throughout the $(k,t_2)$-space, which is to be digitized with a sufficiently short dwell time to characterize both the k- and $t_2$-behavior in a continuous fashion (FIGS. 3A, 3B). Dots in such Figures symbolize the data points digitized during the course of positive and negative acquisition gradients. This oscillatory gradient module is then repeated $N_2$ times, with $N_2$ defining the number of effective points along $t_2$. Processing such set into a spatially-resolved 2D NMR spectrum requires discriminating the signal contained in these points against the two extraction variables $(k,t_2)$. These points do not appear distributed over the regular 2D grid that is needed for carrying out a fast FT along $t_2$, a complication that can be resolved by implementing a separation procedure like the one illustrated in FIGS. 3B, 3C prior to the transform. Separating interleaved data sets in such fashion provides two $S(k,t_2)$ signals displaying a regular spacing between consecutive points, thus being ready for the fast FT. The particular example detailed in the Figure assumes an oscillatory gradient with a square shape; the actual shape, however, is immaterial, and certain instances may arise where alternative shapes (such as sinusoidal modulations) may become more advantageous.

Figure 4:
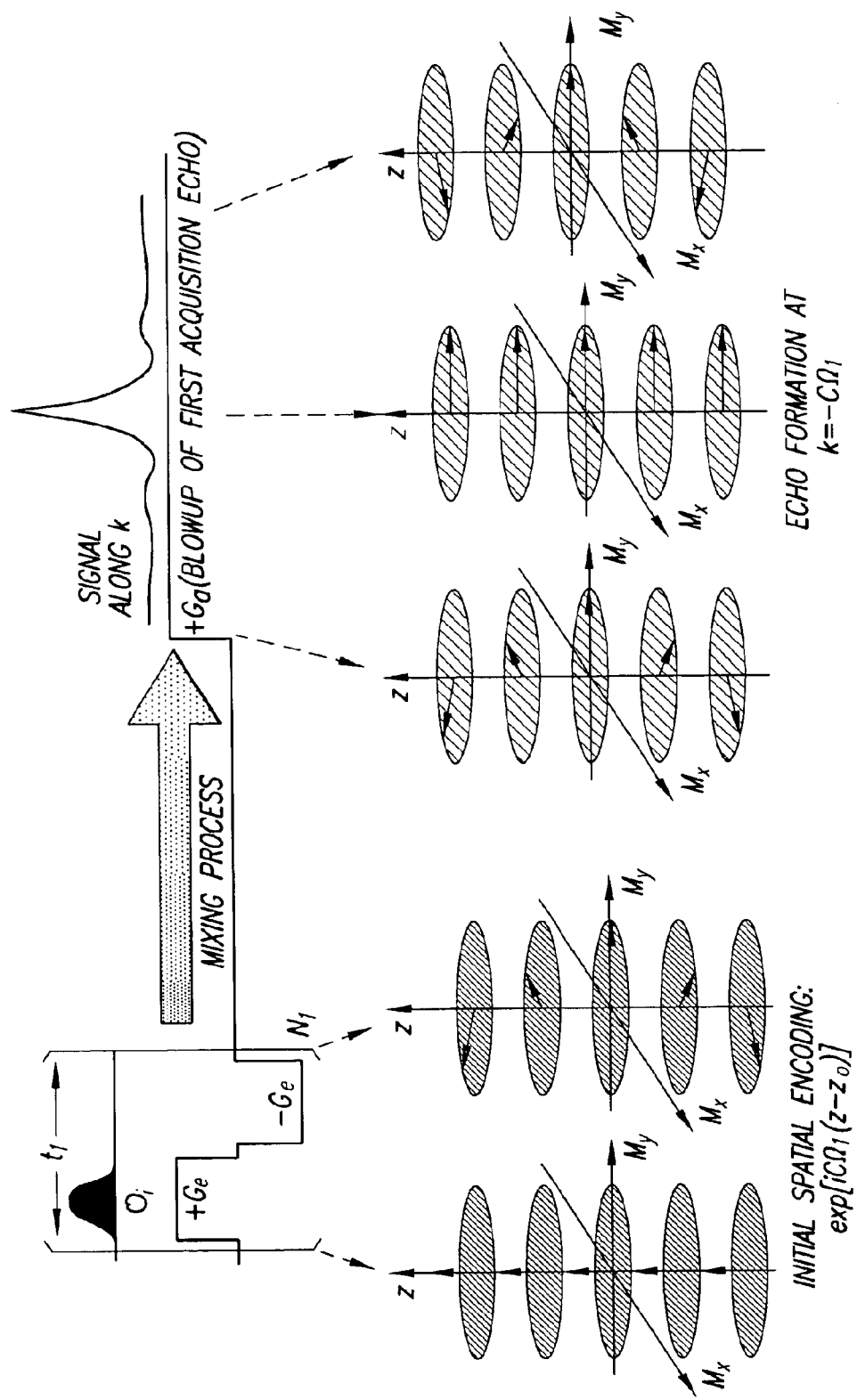
FIG. 4 is a simplified pictorial diagram describing the origin of peaks along the indirect dimensions of ultrafast NMR experiments.

FIG. 4 is a simplified pictorial diagram describing the origin of peaks along the indirect dimensions of ultrafast NMR experiments. The heterogeneous nature of the $t_1$ evolution leads to an encoding of the internal precession frequency $\Omega_1$ along the z axis (second panel from left); this spiral of spin-packets is subsequently unwound by an acquisition gradient $G_a$ possessing an identical z spatial dependence. The coherent addition of spin-packets thus leads to a sharp echo along the k coordinate whose position reveals the extent of $\Omega_1$ encoding prior to the mixing process—in essence, the spectrum along the indirect dimension. Such "peak" formation is only illustrated here for a portion of the first acquisition gradient echo; the phase encoding gained by this echo peak during the course of the $N_2$ gradient-reversals occurring as a function of $t_2$, provides a conventional route to measure the $\Omega_2$ frequencies active during the acquisition.

An odd feature resulting from this 2D NMR data acquisition and processing modes or steps, is the fact that the k axis automatically becomes the $\nu_1$ domain that defines the spins' indirect evolution frequencies. Thus by contrast to conventional 2D NMR, which requires FT against the $t_1$ parameter to characterize the $\Omega_1$ frequencies in the spin system, no FT of the data along the k-axis is needed altogether. This non-conventional processing stems from the fact that in the present invention and in this kind of experiments, peak positions along the indirect domain are not defined via the Fourier analysis of a time-evolving coherence, but via the displacement observed in k-space for the position of an echo created by interfering magnetizations from different slices. A graphical depiction of this aspect or feature is illustrated in FIG. 4, which analyzes the fate of magnetizations, throughout a portion of an ultrafast acquisition assuming a simplified "five-slices" sample. The initial excitation segment of the sequence affects successively the various slices and imposes on them a spatial encoding; yet this encoding will only reflect the initial $\Omega_1$ internal evolution frequency, since the effects of the auxiliary $G_e$ are being compensated by reliance on gradient echoes. The extent of the ensuing evolution can therefore be described for a particular site by a "winding" of its magnetization through the sample, with a pitch dictated by $\exp[iC\Omega_1(z-z_O)]$. This spatial winding is then preserved as either a phase- or an amplitude-modulation throughout the mixing period, with the result that the overall signal available for detection at the beginning of the acquisition will in general be null. At this point, however, a gradient is applied on the sample, whose spatial $$\exp\left[i\gamma_a \int_0^t G_a(t')\, dt'\, z\right]$$

dependence is capable of unwinding the initial spiral of magnetizations. Such unwinding will lead to a constructive interference among the spin-packets corresponding to different slices whenever $$k = \gamma_a \int_0^t G_a(t')dt' = -C\Omega_1,$$

thus decoding the initial evolution frequency that was active during $t_1$ via the location of an echo along the k-axis. This echo makes up the "peak" that will be observed along the indirect domain, whose further evolution as a function of the time $t_2$ is then monitored by successive dephasing and rephasing processes driven by changes in the sign of $G_a$. Hence no additional k-axis FT becomes necessary in order to decode the indirect evolution frequencies active during $t_1$.

Such arguments can be employed to derive a mathematical expression for the observable shapes observed for peak as derived according to the invention or in this kind of experiments. To do so, relaxation and $\Omega_2$ shift effects are neglected in the beginning, and its own individual magnetization vector is associated to each of the $N_1$ discrete slices excited by selective pulses during the course of the initial evolution period. According to the method of the present invention, these spin-packets will end up equally-spaced throughout the sample's length L at positions $$\left\{z_j = \frac{L}{N_1 - 1}[(N_1 - 1)/2 - j]\right\}_{j=0,N_1-1},$$

and contributing with identical weights to the overall S(k) signal that is detected. When acted upon by the acquisition gradient $G_a$, the spin-packets within such discrete slices will be endowed with instantaneous precession frequencies $vj=zj\gamma_a G_a$. The signal originated as a function of $$k = \gamma_a \int_0^t G_a(t')dt'$$

can then be written as $$S(k) = \sum_{j=0}^{N_1-1} F_j e^{ikz_j}. \tag{3}$$

The $\{F_j\}j=0,N_1-1$ coefficients here are a complex set describing the state of the spin-packets at the k=0 instant; they are the x-y magnetizations associated to the various spatial slices, to which is ascribed a j-dependence which accounts for the $\Omega_1$ frequency that may have been active during the initial $t_1$ evolution period. Such spin-packets can consequently be written as $$F_j = \frac{A}{N_1} e^{i\Omega_j t_1(z_j)},$$

A being the overall magnetization expected from a particular site when considered over the whole sample. On the basis of FIGS. 1–3 one can further express the evolution times $t_1$ experienced by magnetizations within each of these slices as $t_1(z_j)=C\cdot(z_j-z_{-1})$, where the $$C = \frac{\Delta t_1 \gamma_e G_e}{\Delta O}$$

coefficient depends on the spacing between consecutive selective excitations. Assuming as done earlier an ideal dwell time $\Delta t_1$ equal to twice the excitation pulse $T_p$ as well as $\gamma_e G_e/\Delta O > 0$ leads to $$C = \frac{2T_p(N_1 - 1)}{L}.$$

Using all these definitions for $z_j$, $F_j$, $t_1$ and C, it is possible to rewrite eq. (3) as $$S(k) = \frac{A \cdot e^{iT_p(N_1+1)\Omega_1}}{N_1} \cdot e^{i\varepsilon/2} \cdot \sum_{j=0}^{N_1-1} [e^{-i\varepsilon/(N_1-1)}]^j \tag{4}$$

where $\varepsilon = 2\Omega_1 T_p(N_1-1) + kL$. The geometric series in eq. (4) can be evaluated using the well-known relation $$\sum_{j=0}^{N-1} z^j = (1 - z^N)/(1 - z),$$

leading to $$S(k) = \frac{A \cdot e^{iT_p(N_1+1)\Omega_1} e^{i\varepsilon/2}}{N_1} \cdot \frac{1 - e^{-i\varepsilon N_1/(N_1-1)}}{1 - e^{-i\varepsilon/(N_1-1)}}, \tag{5}$$

which can also be rewritten as $$S(k) = \tag{6}$$

$$\frac{A \cdot e^{iT_p(N_1+1)\Omega_1}}{N_1} \cdot \frac{e^{i\varepsilon/2} e^{-i\frac{1}{2}\varepsilon N_1/(N_1-1)}}{e^{-i\frac{1}{2}\varepsilon/(N_1-1)}} \cdot \frac{e^{i\frac{1}{2}\varepsilon N_1/(N_1-1)} - e^{-i\frac{1}{2}\varepsilon N_1/(N_1-1)}}{e^{i\frac{1}{2}\varepsilon/(N_1-1)} - e^{-i\frac{1}{2}\varepsilon/(N_1-1)}}.$$

As the ratio in the middle of this expression is unity, eq. (6) yields $$S(k) = \frac{A \cdot e^{iT_p(N_1+1)\Omega_1}}{N_1} \cdot \frac{\sin\left[\frac{1}{2}\varepsilon N_1/(N_1-1)\right]}{\sin\left[\frac{1}{2}\varepsilon/(N_1-1)\right]}. \tag{7}$$

On considering $N_1 \gg 1$ we have $N_1+1 \approx N_1$, $N_1/(N_1-1) \approx 1$ and $1/(N_1-1) \approx 1/N_1$; using these approximations and replacing back for $\varepsilon$'s expression results in the relatively simple line shape expression $$S(k) = \frac{A e^{iT_p N_1 \Omega_1}}{N_1} \cdot \frac{\sin\left(\Omega_1 T_p N_1 + \frac{kL}{2}\right)}{\sin\left(\Omega_1 T_p + \frac{kL}{2N_1}\right)}. \tag{8}$$

These equations also enable a derivation of basic Nyquist criteria for the new acquisition step or scheme. Denoting $T_a$ as the duration during which $\pm G_a$ gradients are applied and $\Delta t$ as the actual physical dwell time (FIG. 3) leads to $N_k = T_a/\Delta t$ complex points being collected along the k-axis. Assuming then that the $\pm G_a$ cycle is repeated $N_2$ times, results in a $2T_a N_2$ total digitization time for the step or experiment and in $2N_2 N_k$ complex points being collected overall. Points following the data separation procedure will be spaced along $t_2$ by $2T_a$ intervals, leading to $SW_2 = (2T_a)^{-1}$ spectral widths along the direct domain. The maximum range that under such conditions will be scanned along the k-axis is $k_{max} = \gamma_a G_a T_a$, which will in turn enable peaks to be accommodated over a $SW_1 = |k_{max}/C|$ spread along the indirect domain. The constant C is given by the ratio between the extent of $t_1$ evolution and the degree of spatial z encoding: $C=\Delta t_1/\Delta z=\Delta t_1/[\Delta O/\gamma_e G_e]$, $\Delta t_1$ being the time between one excitation pulse and the next, $\gamma_e G_e$ the gradient's strength during excitation, and $\Delta O=|O_{i+1}-O_i|$ the constant increment used to offset the selective excitation pulses. Under the idealized scheme in FIGS. 1–3 $\Delta t_1 \approx 2T_p$, twice the selective pulses' duration; C is then $2T_p\gamma_e G_e/\Delta O$ and the overall indirect spectral width becomes (in frequency units)

$$SW_1 = \left|\Delta O \frac{\gamma_a G_a T_a}{2\gamma_e G_e T_p}\right|.$$

These expressions for $SW_1$ and $SW_2$ are of practical quantitative use, provided that corrections are made for the gradients' non-idealities. These arguments also predict that, at least under ideal conditions, purely absorptive line shapes are built-in features of ultrafast NMR experiments. Indeed peaks along the indirect dimension form as a result of the constructive interference among spin-packets distributed along the rectangular $\rho(z)$ profile of the sample container. Leaving potential distortions arising from the selective excitation and the spin relaxation aside, this will lead to peaks possessing sinc-type point-spread functions and thus no dispersive component. When convoluted with the normal Absorptive$(v_2)$+i·Dispersive$(v_2)$ line shape resulting along the direct domain after FT$(t_2)$, a 2D sinc$(v_1)$·Absorptive$(v_2)$ kernel possessing convenient site-resolving characteristics will characterize peaks in this kind of spectra.

Figure 5A:
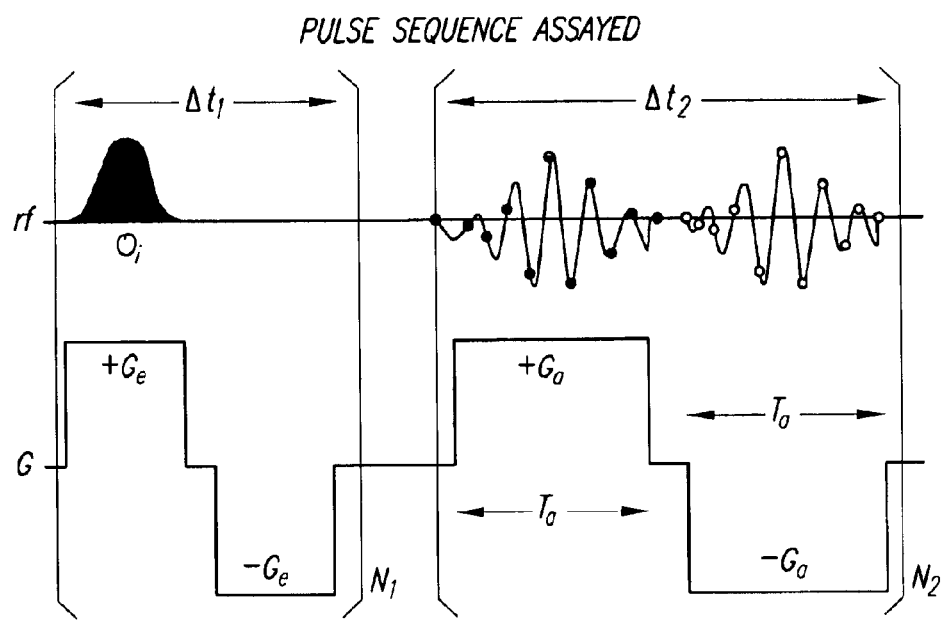
FIGS. 5A–G show graphically and pictorially the data acquisition and processing stages involved in the retrieval of ultrafast NMR experiments on a chemical sample.
Figure 5B:
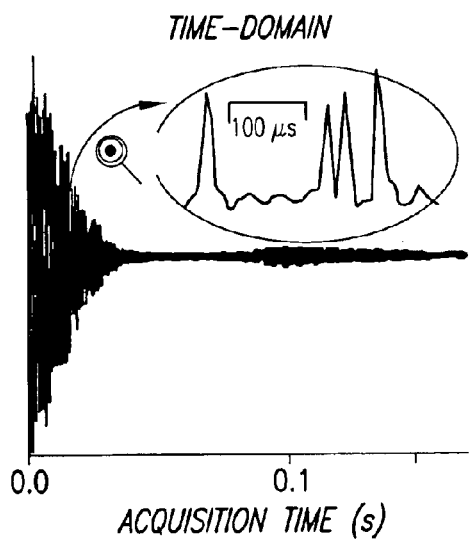
Figure 5C:
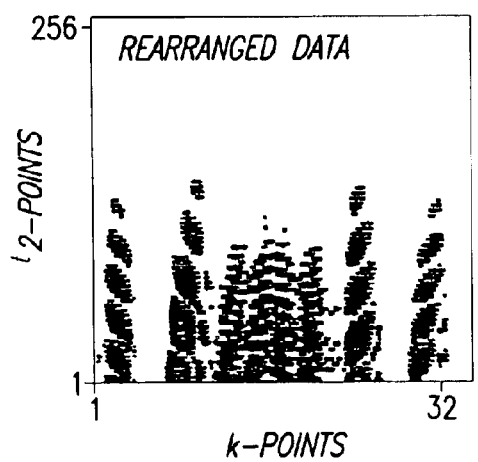
Figure 5D:
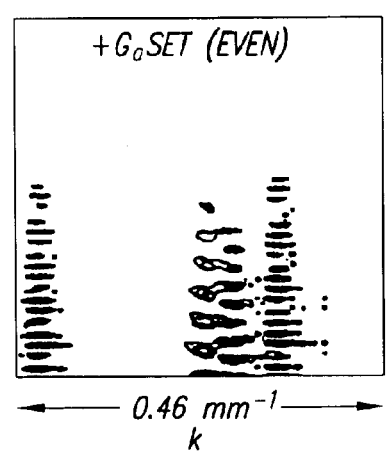
Figure 5E:
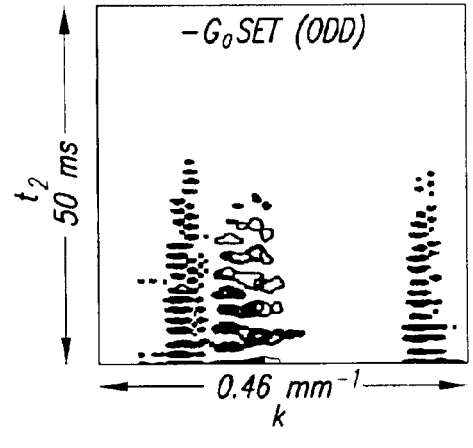
Figure 5F:
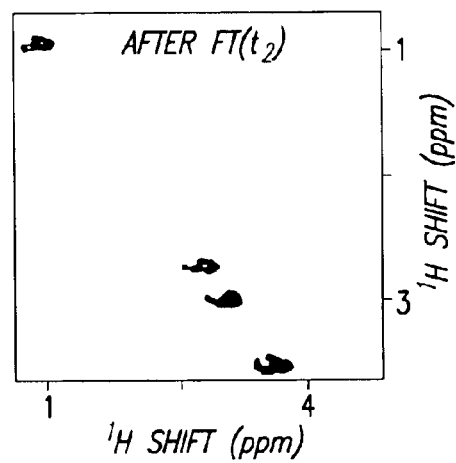
Figure 5G:
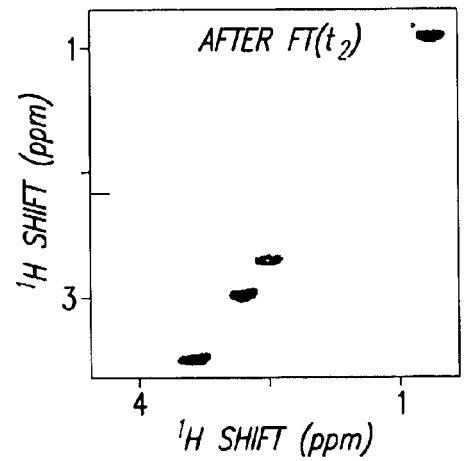

FIGS. 5A to 5G illustrate and show graphically and pictorially the summary of events involved in the single-scan acquisition of phase-sensitive 2D NMR spectra, illustrated with $^1$H data recorded on a solution of n-butylchloride dissolved in CDCl$_3$ and utilizing a 2D NMR sequence devoid from actual mixing process. In FIG. 5A time-domain data is collected using the spatially-selective excitation/detection procedures illustrated in FIGS. 2B and 3A. In FIG. 5B, the magnified inset shows the signal (magnitude) arising from an individual $T_a$ period, depicting in essence the compound's unidimensional $v_1$ spectrum. In FIG. 5C, a 2D contour plot of the unidimensional data set illustrated in FIG. 5B, following a rearrangement of its $2N_kN_2$ points according to their k and $t_2$ coordinates according to the procedure given in FIG. 3B. Interleaved data sets acquired with $+G_a$ and $-G_a$ gradients are still present at this point, thus resulting in a mirror-imaging of the signal along the k-axis. FIGS. 5D and 5E show pairs of data sets resulting upon separating the interleaved $+G_a/-G_a$ arrays in (C) into two (k,$t_2$) signals possessing $N_kN_2$ points each, as illustrated in the process leading from FIG. 3B to FIG. 3C. The signals shown in these sets have been subject to a phase correction and to a minor shearing that compensates for non-idealities in the acquisition gradient strengths (see below). The spectral structure observed already at this point along the k axis is noticeable. FIGS. 5F and 5G show mirror-imaged 2D NMR spectra arising upon subjecting the data sets in FIGS. 5D and 5E to $t_2$ Fourier transformation. The k-axes of FIGS. 5D and 5E automatically become the $v_1$ axes of these spectra.

As described above, FIGS. 5A to 5G illustrates a basic 2D $^1$H NMR acquisition on an n-butylchloride sample, using a 2D test pulse sequence (FIG. 5A) that actually involves no mixing process or step as an example of the data processing required by the methodology of the present invention. Identical frequencies have here been active throughout the evolution and acquisition times, and only diagonal peaks result. As in all ultrafast experiments that will be later reported these data were collected as an unidimensional set, which when magnified appears to be composed by a series of 1D indirect-domain NMR spectra (FIG. 5B). This is a reflection of the method's built-in capability to FT the signal that was encoded during $t_1$, via the $G_a$ gradient defining the k-axis. Processing continues with the assembling of the S(k,$t_2$) 2D data set (FIG. 5C) followed by the separation of the points corresponding to alternate $+G_a/-G_a$ acquisitions, whose onwards processing is carried out independently (FIGS. 5D, 5E). A recursive artifact that may arise in ultrafast 2D NMR data sets consists of a "tilting" of the k-space peaks, when followed as a function of time $t_2$. This artifact grows as the intensity and/or duration of the gradients used in the experiment increases, and numerical simulations further detailed below suggest that it arises from a small weakening in the gradients' absolute value as a function of the acquisition time $t_2$ ("gradient drooping"). Rather than compensating for this effect instrumentally, it can be corrected via a numerical shearing of the data. If purely absorptive line shapes are desired, processing continues after this stage by the phasing of the $t_2$=0 slice, a copying of such phase correction through all $t_2$ values, and a Fourier transformation of the data as a function of $t_2$ to yield the final 2D spectrum (FIGS. 5F, 5G). Though not implemented for this data set, weighting and zero-filling can also be applied along the k-axis in a procedure that includes ancillary transformations of the data to and from their conjugate z-domain. As a result of all this processing, one obtains two sets of 2D (k, $v_2$) data; essentially two NMR spectra, which are mirror-imaged to one another as a result of the opposing gradients employed in the scanning of their k-axes. It is thus possible to improve the overall S/N by reversing one of these sets and then combining them both into a single 2D NMR spectrum. As the $+G_a$ and $-G_a$ gradients defining these data sets are rarely of identical magnitudes, care should be exercised in this procedure and the coincidence of peaks in the two sets should be ensured prior to their recombination.

The 2D NMR data in FIGS. 5A to 5G arise from a sequence deprived of a real mixing process, and hence its peaks are arranged solely along the main homonuclear diagonal. FIGS. 6A to 6D compare graphically and pictorially between single-scan (FIGS. 6A and 6B) and conventional (FIGS. 6C and 6D) 2D phased data sets acquired on an n-butylchloride/CDCl$_3$ sample. Schematics of the COSY and TOCSY sequences utilized in these experiments are shown on the left- and right-hand side panels, respectively. The structure of the molecule, indicating its proton sites' shifts (in ppm), is also shown on top for ease of analysis. All data were acquired on a Bruker® DMX500 NMR spectrometer using a Nalorac® TXI probehead, and for each case the experiment's approximate duration is indicated. For the single-scan acquisitions $N_1$=40 initial Gaussian pulses were applied at 4 kHz offset increments while in the presence of $\gamma_e G_e$=150 kHz/cm, while the acquisition involved $N_2$=256 gradient echoes with $T_a$=340 µs and 10 µs dwell times. All remaining pulses were applied non-selectively. Conventional 2D NMR experiments involved a TPPI phase cycle with 16 scans/$t_1$ point and 8 dummy scans.

The comparison shown in FIG. 6 illustrates the contrast between conventional and ultrafast 2D NMR spectra for the model compound when subject to two "real" 2D NMR sequences: COSY, correlation spectroscopy, which correlates cross-peaks among directly coupled neighbors, and TOCSY, total correlation spectroscopy, which establishes cross peaks among the full system of mutually-coupled spins, see for example R. R. Ernst, G. Bodenhausen and A. Wokaun, "Principles of Nuclear Magnetic Resonance in One and Two Dimensions" Clarendon, Oxford, 1987, and H. Kessler, M. Gehrke and C. Griesinger, *Angew. Chem. Int. Ed. Engl.* 27, 490 (1988). As can be appreciated from FIGS. 6A to 6D, both normal and fast acquisition schemes convey an identical spectral information, though in radically different amounts of experimental time. The spatial encoding principles illustrated so far for monitoring 2D homonuclear connectivities, can also be employed for implementing heteronuclear correlations. Application of the invention in this respect or such experiments will rely on applying the $\Omega_1$-driven spatial winding of magnetizations on a particular spin species S, preserving this encoding as an amplitude modulation during a mixing which implements a heteronuclear S→I transfer, and then decoding this information during the acquisition by gradients applied on the second I species.

Figure 7A:
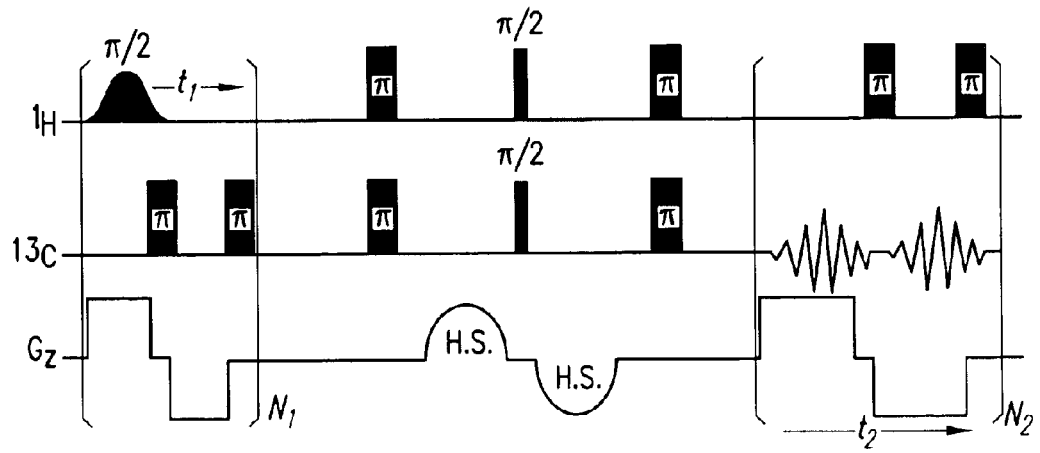
FIGS. 7A–D are similar to FIG. 6, but for cases involving two different kinds of heteronuclear 2D correlations: (A) with direct detection; (B) with indirect detection.
Figure 7B:
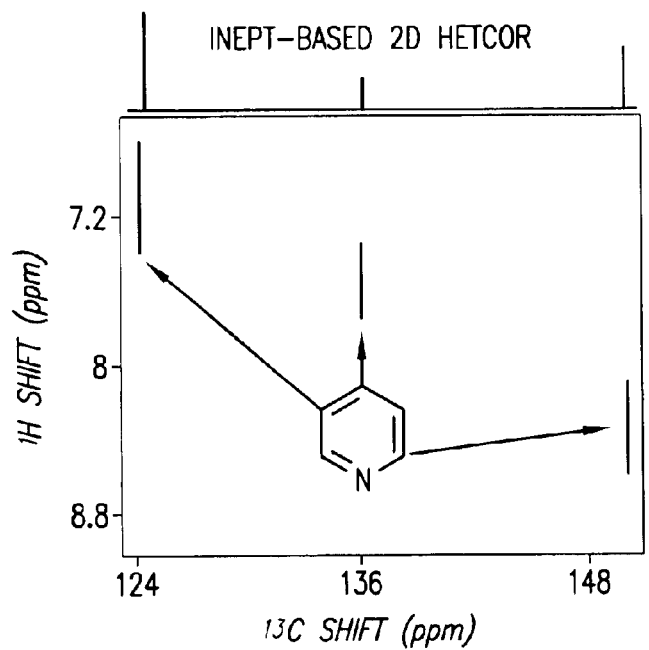
Figure 7C:
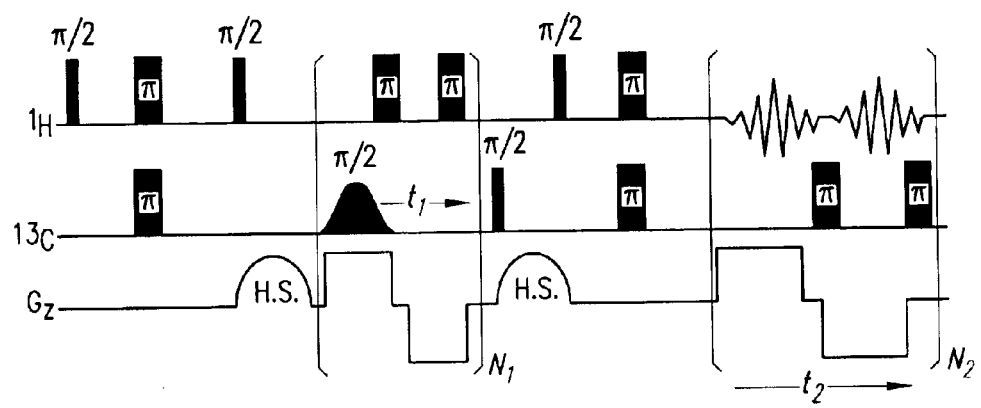
Figure 7D:
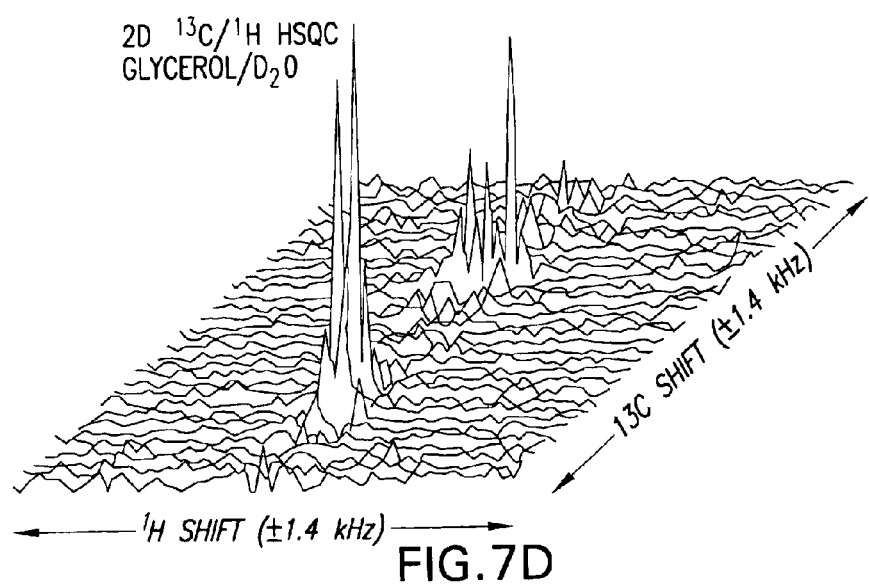

FIGS. 7A, 7B, 7C and 7D show examples where 2D correlations are established between different kind of nuclei. FIGS. 7A and 7B show a 2D $^1H$-$^{13}C$ single-scan NMR spectrum obtained on a pyridine/CDCl$_3$ sample using the directly-detected heteronuclear correlation sequence sketched on top, which involves a spatial encoding of the $^1H$ magnetization and subsequent decoding on the $^{13}C$ channel. Data acquisition parameters included $N_1$=33, $N_k$=29, $N_2$=360, $\Delta O$=4 kHz, $\gamma_e G_e$=38 kHz/cm, $\gamma_a G_a$=50 kHz/cm, 256 $\mu$s Gaussian excitation rf pulses, 5 $\mu$s dwell times and homospoil (H.S.) gradients tuned to select the $H_xC_z$→$H_zC_x$ coherence transfer. The total acquisition time was in this case ≈200 ms; other details are as in FIG. 6. In FIGS. 7C and 7D, a 2D $^1H$-$^{13}C$ pure-phase NMR spectra obtained on the indicated sample at natural abundance, using the indirectly-detected heteronuclear single-quantum correlation (HSQC) type sequence sketched on top. Data acquisition details included $N_1$=20, $N_k$=32, $N_2$=128, $\Delta O$=4 kHz, $\gamma_e G_e$=40 kHz/cm, $\gamma_a G_a$=97 kHz/cm; other details are the same as mentioned in conjunction with FIGS. 6A to 6D. Two scans with the selective $^{13}C$ pulse (and the receiver) phase-cycled by 180° were collected for the sake of removing residual $^1H$-$^{12}C$ background signals.

FIG. 7 illustrates how two sequences that form the basis of several directly- and indirectly-detected heteronuclear correlation experiments, see for example R. R. Ernst, G. Bodenhausen and A. Wokaun, "Principles of Nuclear Magnetic Resonance in One and Two Dimensions" Clarendon, Oxford, 1987; H. Kessler, M. Gehrke and C. Griesinger, *Angew. Chem. Int. Ed. Engl.* 27, 490 (1988); J. Cavanagh, W. J. Fairbrother, A. G. Palmer III and N. J. Skelton, "Protein NMR Spectroscopy: Principles and Practice" Academic Press, San Diego, 1996; and M. Levitt, "Spin Dynamics" John Wiley & Sons, New York, 2001, can be modified for their single-scan execution according to the present invention. The first of these sequences is based on a $^1H$ $t_1$ evolution followed by an INEPT-based transfer period; the fact that $t_1$ in this sequence is triggered by a simple 90° excitation, enables the introduction of a spatial-encoding in ways that are entirely parallel to the ones implemented in the homonuclear correlations (FIGS. 7A and 7B). The only major distinction with the conventional 2D sequence then arises from the inability of conventional decoupling sequences to achieve their aim while under the action of intense oscillating gradients. Such goals were consequently implemented during both the $^1H$ and $^{13}C$ free evolution periods, by inserting 180° pulses within the complementary RF channel during the course of the +G/−G transition delays. The same decoupling principle was incorporated in the second of the heteronuclear correlation sequences assayed, HSQC (FIGS. 7C and 7D). By contrast to its directly-detected counterpart this sequence begins with a multi-pulse refocused INEPT block that is not susceptible to a simple spatial encoding. Still a spatial winding of magnetizations could be incorporated by shaping the 90° pulse that triggers the $H_zC_z$→$H_zC_x$ conversion, and with it the $t_1$ evolution, following the first INEPT block.

Figures 8A, 8B:
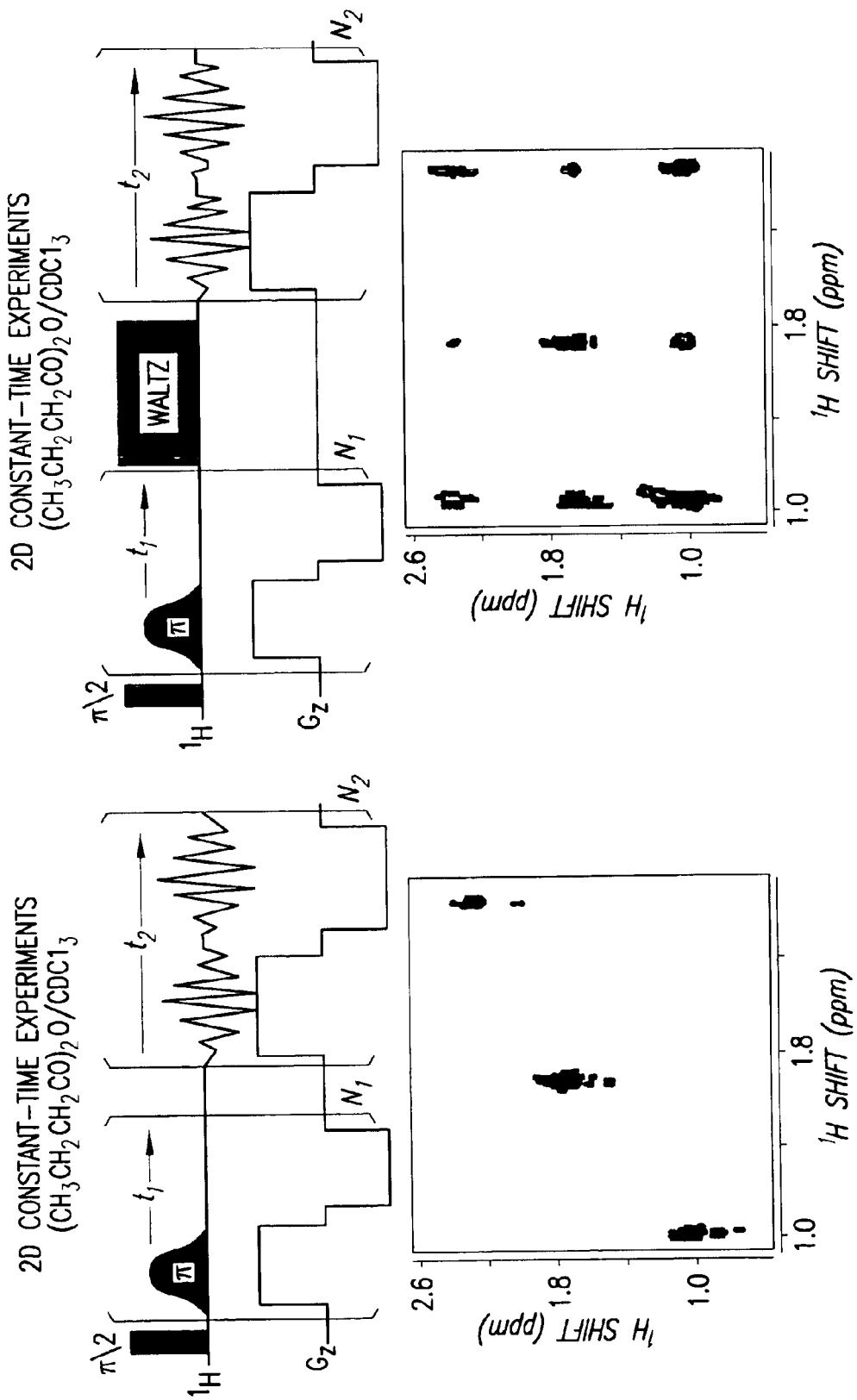
FIGS. 8A–B illustrate the inventive method's capability to the implementation of constant-time 2D NMR experiments, using simple pulse sequences as examples.

In addition to a stepwise $t_1$ incrementation, a common NMR approach to encode indirect evolution frequencies relies on systematically varying the location of a 180° pulse through the duration of a constant evolution period $\tau$, see for example Ernst et al and Kessler et al cited above. Such pulse will refocus the linear evolution terms (chemical shifts and heteronuclear couplings) yet leave homonuclear couplings unaffected, thus providing an appealing option to achieve homonuclear decoupling. The spatial encoding scheme introduced according to this invention can also be incorporated into this so-called constant-time modality, as illustrated by the example shown in FIGS. 8A and 8B. FIGS. 8A and 8B show a 2D pure-phase single-scan $^1H$ NMR spectra collected on a CDCl$_3$ solution of butyric anhydride, using the constant-time modality sequences schematized on top of each contour. Data acquisition details included $N_1$=26, $N_k$=65, $N_2$=160, $\Delta O$=4 kHz, $\gamma_e G_e$=77 kHz/cm, $\gamma_a G_a$=46 kHz/cm, dwell time=8 $\mu$s, 400 $\mu$s Gaussian 180° pulses. FIG. 8A shows a mixing-less pulse sequence, showing the three nonequivalent proton sites in the molecule aligned along the main diagonal. FIG. 8B is idem but incorporating a 50 ms long isotropic mixing period, leading to cross peaks among all mutually coupled protons (right).

This ultrafast scheme achieves a spatial encoding not by incrementing the initial excitation pulse but by using a single 90° excitation, which is subsequently followed by a train of spatially-selective 180° refocusing pulses. An $\exp[i\Omega_1(\tau-2Cz)]$ shift-driven winding of magnetizations is then imposed on the sample, from which the $v_1$ frequency spectrum can be decoded via the k-space protocol just as described before. As illustrated by the butyric anhydride example shown in FIGS. 8A and 8B purely absorptive line shapes are again a possibility in this kind of acquisition mode.

A particular class of 2D NMR experiments or applications are those underlying the acquisition of 2D magnetic resonance imaging (MRI). 2D MRI is, arguably, the most widely executed kind of NMR experiment, see for example M. A. Brown and R. C. Semelka, "MRI: Basic Principles and Applications" New York, 1999, yet from a spectroscopic standpoint it is actually a particular case of the much wider world of 2D NMR, see for example Ernst et al cited above. The main difference between conventional 2D NMR and 2D MRI applications or experiments is that whereas in the former the interactions to be correlated are purely internal, for instance couplings or shifts, the latter tends to neglect these for the sake of monitoring an artificial interaction given by the application of an external gradient in the magnetic field. Field gradients are also integral constituents of the spin evolution periods of the ultrafast scheme in FIGS. 1A and 1B, yet particular care is taken in this sequence to remove their effects via systematic changes in their sign and the ensuing generation of gradient echoes devoid of imaging information. If, however, these gradients oscillations were to be removed, the same acquisition scheme would become useful for the ultrafast acquisition of 2D MRI sequences.

Figure 9A:
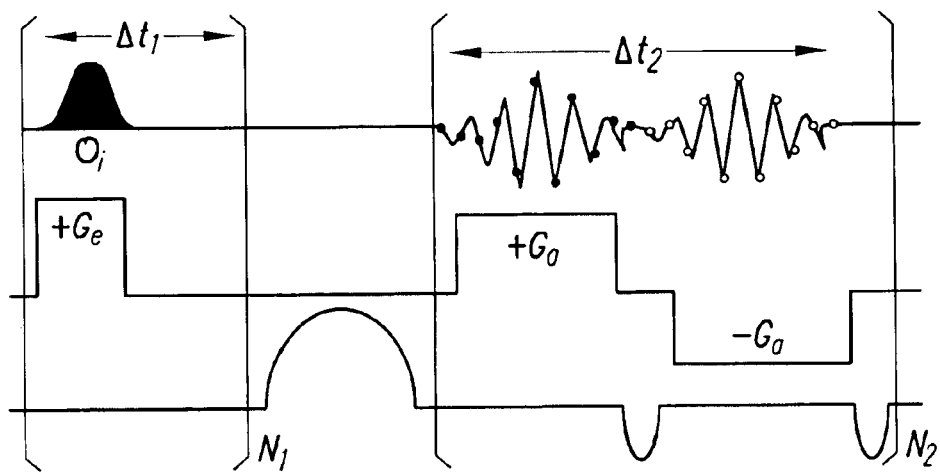
FIGS. 9A–E illustrate the applicability of the inventive method to the acquisition of 2D NMR images (pure 2D MRI).
Figure 9B:
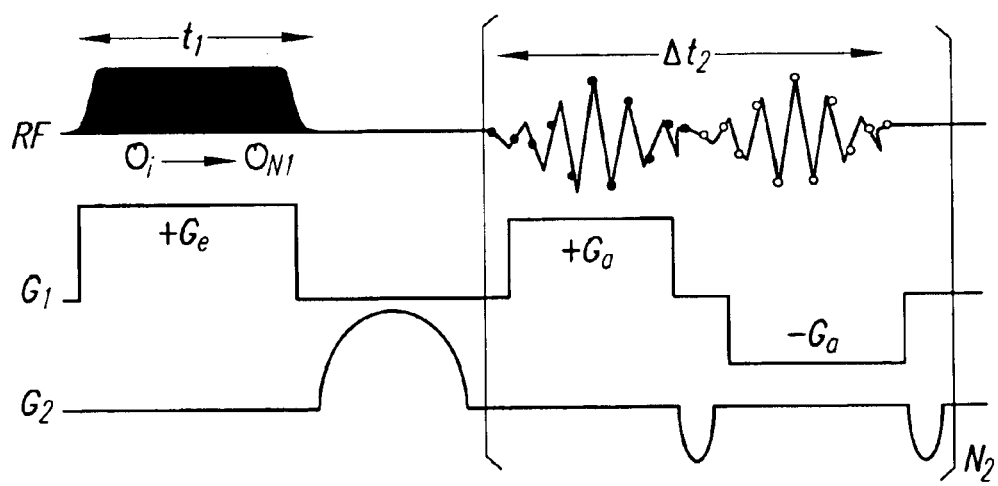
Figure 9C:
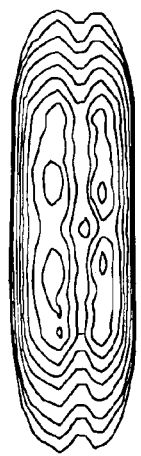
Figure 9D:
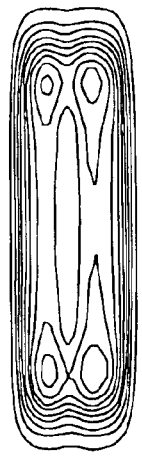
Figure 9E:
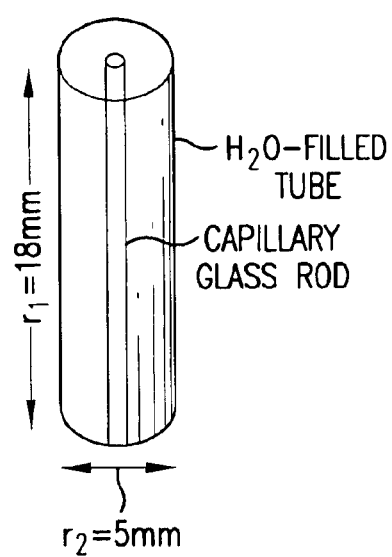

FIGS. 9A to 9E show the adaptation and exemplification of how the new inventive method can be employed to collect 2D NMR images (pure 2D MRI) within a single scan. FIG. 9A shows the modifications implemented on the basic spectroscopy scheme given in FIG. 5A, whereby the position of the spins becomes encoded by removing the gradient echo refocusing from the excitation process. The net result is a train, of $N_1$ frequency selective pulses, applied while in the presence of an intermittent gradient. FIG. 9B shows a pulse sequence resulting upon taking the $G_e$ "off" period in FIG. 9A to zero; the consequence is a continuous, highly efficient RF pulse whose offset varies linearly between $O_1$ and $O_{N1}$. FIGS. 9C and 9D show 2D $^1$H MRI images obtained using the pulse sequences illustrated in FIGS. 9A and 9B, and reflecting as contour plots the water location profile used in the phantom that was experimentally tested (shown in the center for the sake of comparison), see FIG. 9E.

FIG. 9A illustrates the basic single-scan 2D MRI experiment that would result from implementing these changes, with $\Omega_1$ becoming now associated with a position-dependent frequency $G_1 r_1$ and $\Omega_2$ encoding a position-dependent frequency $G_2 r_2$ (with $r_1$ and $r_2$ reflecting any pair of x, y or z orthogonal directions). Furthermore, as no need for waiting for a refocusing $-G_e$ delay is now needed after each initial RF excitation pulse, the possibility arises of employing a continuous, windowless train of variable-frequency RF pulses over the course of $t_1$. FIG. 9B presents the pulse sequence resulting when taking this concept to the limit of very short pulse widths; a single chirp pulse where frequency offsets are continuously swept between $O_1$ and $O_{N1}$ then results, capable of carrying out the spins' excitation in a very efficient and robust manner. As illustrated with the test images presented in FIGS. 9C and 9D, either of these schemes is capable of affording 2D MRI images in a single, ultrafast scan. In this respect the abilities of this scheme are comparable to those of echo-planar imaging (EPI), a fundamental MRI tool that is also capable of affording 2D images within a single scan, see for example P. Mansfield, J. Phys. C: Solid State Phys. 10, 55 (1977), and M. K. Stehling, R. Turner and P. Mansfield, Science 254, 43 (1991). The principles of operation underlying these two methods are, however, entirely different, with the new spatial-encoding approach of the present invention as applied to 2D MRI deriving from a general methodology capable of speeding up any 2D NMR sequence.

Besides the application just described to MRI the invention provides a second route to obtain localization insight, this time via the spatial distribution information that resides in the shape of the spectroscopic echo peaks that are observed along the indirect k domains. To analyze this localization feature we focus on a particular $(\Omega_1, \Omega_2)$ peak, and examine the one-dimensional line shape that it will exhibit along the $k/v_1$-axis as a function of the displacement $\Delta k$ from the $k=-C\Omega_1$ condition. Using the bracketed summation in eq. (3) as starting point, leads then to $$S(\Delta k) = e^{-iC\Omega_1 z_{N_1}} \sum_{j=0}^{N_1-1} A(z_j) e^{i\Delta k z_j}. \quad (9)$$

Figure 10:
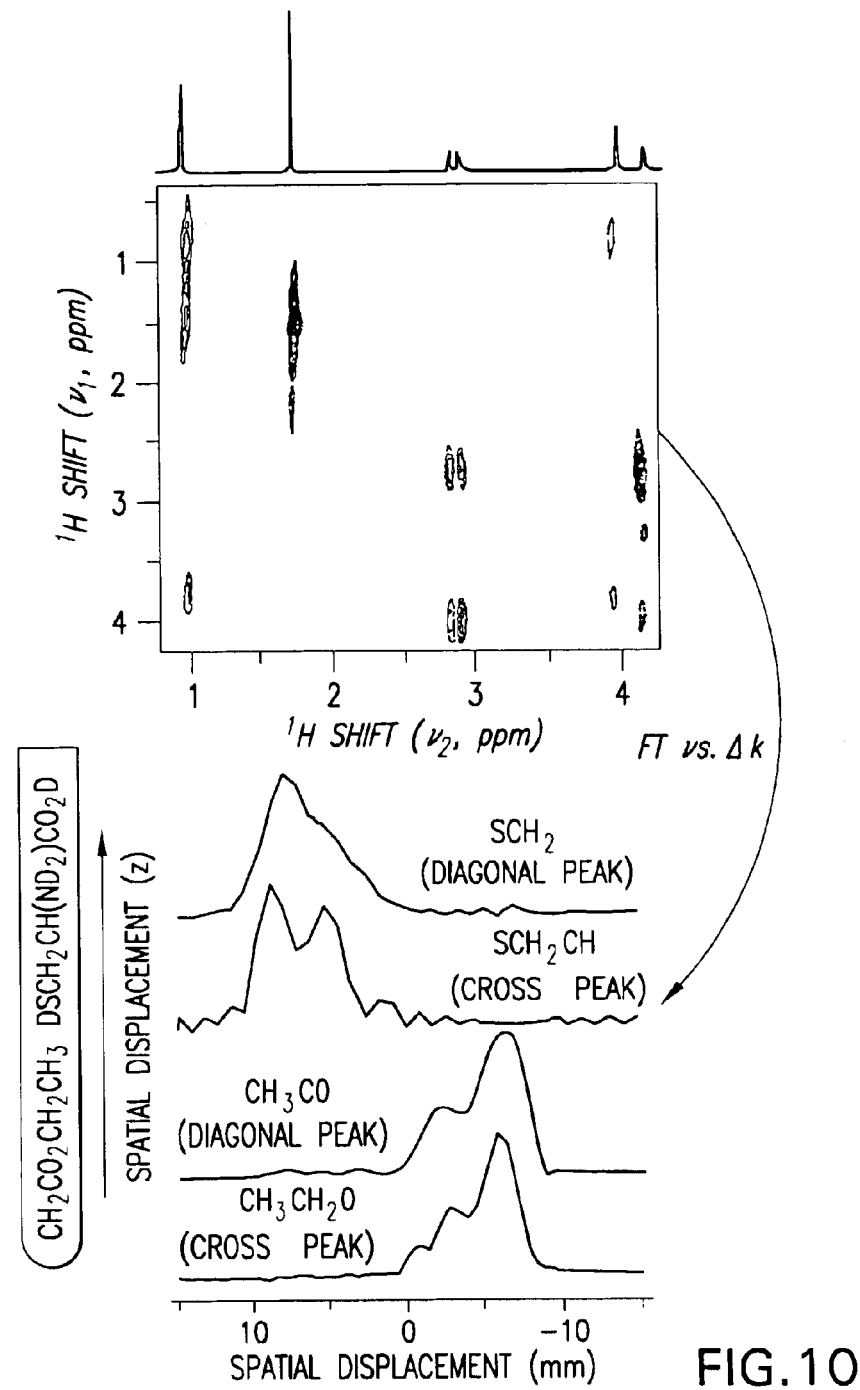
FIG. 10 illustrates the possibility of the invention to retrieve both spectral and spatial multidimensional information, from the same single-scan sub-second acquisition (spatially-resolved 2D NMR/MRI)

The $e^{-iC\Omega_1 z_{N_1}}$ factor in this equation arises from the non-coincidence assumed between the z=0 sample coordinate and the $t_1=0$ condition, and if so desired could be corrected away via an appropriate first-order phase correction. Aside from this artificial factor one recognizes in the $S(\Delta k)$ function a Fourier conjugate of the spins signal amplitudes throughout the sample's z profile. These amplitudes—proportional in turn to the spins' z density weighted by the various spin relaxation processes that might have been active throughout the pulse sequence—can therefore be extracted via a Fourier analysis of the signal's line shape as a function of $\Delta k$. For instance when dealing with a homogeneous cylindrical sample and in the absence of spin relaxation, $S(\Delta k)$ will display the Sinc-type dependence derived from eq. (8); Fourier analysis of this point-spread function against $\Delta k$ will naturally reflect the square sample profile that originated it. In more general cases, a similar ancillary $FT(\Delta k)$ procedure on each $(\Omega_1, \Omega_2)$ resonance would allow one to obtain the spatial distribution profile of the spins that lead to the formation of that particular peak. A most appealing aspect of such an approach is that spatially-localized information can thus be achieved without really demanding any additions or modifications to the original single-scan 2D NMR spectroscopy experiment. All that is needed is extracting a suitable complex data array defining the full extent of a chosen peak along the $k/v_1$ axis, and subjecting it to Fourier analysis. FIG. 10 illustrates this mode of operation, with a set single-scan 2D $^1$H NMR results recorded on the polar compound L-cysteine hydrochloride (8 mg) dissolved in an aqueous phase, and coexisting with an organic solution of ethyl acetate (5 $\mu$L) dissolved in $CCl_4$. An isotropic recoupling sequence was incorporated during the course of the mixing leading to the single-scan acquisition of a 2D TOCSY NMR spectrum for the two solutes. Cross-peaks in this spectrum were sufficiently resolved to enable a spatial characterization of the analytes' distributions by means of their individual $FT(\Delta k)$ line shapes; the resulting profiles clearly show the spatial separation of the two phases for all the diagonal- and cross-peaks chosen for analysis.

Technical aspects worth discussing are the spatial range and resolution that will characterize this kind of spatially-resolved 2D spectral protocols. These will actually follow from the spectral width (SW) characteristics of single-scan 2D NMR experiments; for the basic setup summarized in the preceding paragraphs, their values along the indirect and direct domains have been shown given by $$SW_1 = \left| \Delta O \frac{\gamma_a G_a T_a}{\gamma_e G_e \Delta t_1} \right|,$$

$SW_2 = (2T_a)^{-1}$ respectively. The spatial characteristics that follow from the Fourier analysis of peaks along the $k/v_1$-domain can be then worked out from coupling these SW considerations to the spectral characteristics of the analyzed metabolites, which will in turn dictate the maximum range of k values that can be used in the FT of any given peak. Indeed assuming that a peak to be Fourier analyzed along the indirect $k/v_1$-domain is resolved from other peaks along the same axis by a $\Delta v$ frequency span, will enable data points to be transformed over a maximum range of $$\Delta k_{max} = \left| \frac{\Delta v \gamma_e G_e \Delta t_1}{\Delta O} \right|.$$

For the typical $^1$H NMR parameters expected in a microscopy setting and at moderate magnetic field strengths ($\Delta v \approx 0.5$ kHz, $\Delta O \approx 5$ kHz, $G_e \approx 10$ G/cm, $\Delta t_1 \approx 1$ ms) this will lead to a spatial resolution in the order of 0.2 cm. The associated field of view will in turn be given by the number of points sampled within each $T_a$ interval; typical dwell time values lead then to spatial fields in the 2–4 cm range. The overall order of magnitude of these two spatial parameters can be expected to increase or decrease by a decade upon switching the experiment to whole-body or microimaging conditions respectively; in either case, this simple analysis reveals that there is an appropriate window of opportunity where both spectral and spatial information can be extracted from single-scan experiments.

The present description has focused so far on the use of spatial encoding methods and protocols to accelerate the acquisition of various 2D NMR experiments. The invention employs the same principles for acquiring higher-dimensional NMR spectra within a single scan, a particularly important goal given the exponential increase that the duration of N-dimensional NMR experiments exhibit with respect to N. A relevant point to notice in order to proceed with the extension of the new ultrafast acquisition invention to higher dimensionalities, are the dissimilar roles that the gradient's strength and the gradients geometry play in the collection of the data. As evident from the arguments above, the strengths $G_e$, $G_a$ will define important range and resolution characteristics of the single-scan 2D NMR spectrum. The actual geometrical distribution of the gradient by contrast, is mostly responsible for relatively minor line shape characteristics related to the sharpness of the echo formation. Indeed most of the arguments described in the preceding discussion would remain equally valid if the gradient used to encode and decode the $\Omega_1$ frequencies were assumed applied along the x (or y) rather than along the z direction. In either case, a spiral of spin-packets would be created by the selective excitation protocol illustrated in FIG. 1, even if for a cylindrical profile the use of radial (x or y) gradients would end up giving different relative weights A(r) to the various spin-packets into which the sample is partitioned. In fact the only demand that the performance of this kind of experiments places on a gradient's geometry, is that it should generate a spiral of spin-packets that is convoluted enough to result in a null magnetization when considered over the whole sample. In principle there are infinite gradient geometries capable of fulfilling such conditions, including among others those represented by the boundless $\{Y_{l,m}\theta,\phi\}$ series of real spherical harmonics of the kind present in modern high resolution NMR shim systems, see for example M. J. E. Golay, *Rev. Sci. Instr.* 29, 313 (1958). Thus if assuming a generalized field gradient possessing $Y_{l,m}$ spatial dependence and $G=\partial B_O/\partial(Y_{l,m})$ strength, all arguments leading to eq. (3) can be repeated to derive a macroscopic magnetization that at the conclusion of the $t_1$ evolution period will be summarized as $$M(N_1 \Delta t_1) = \int_x \int_y \int_z A(x, y, z) \cdot e^{iC\Omega_1(Y_{l,m} - Y^o_{l,m})} dx\,dy\,dz. \quad (9)$$

This equation represents a winding of spin-packets, arranged this time along the gradients $Y_{l,m}$ geometry and possessing non-uniform A(x,y,z) weights. Such winding will once again lead to an overall zero magnetization when considering an $\Omega_1$ chemical shift evolution and integration over the whole sample. The same $Y_{l,m}$ gradient used to achieve the spatial encoding in eq. (9), however, holds the key for unwinding this spiral of spin-packets, and consequently, for the generation of an observable echo during the course of the acquisition. In order to achieve this unwinding, spins should be allowed to accumulate a phase exp(ik·$Y_{l,m}$), with k=$\gamma_a \int G_a(t)dt = -C\Omega_1$ during the course of each acquisition dwell time $\Delta t_2$. Just as in the z example above, this will again allow one to map the evolution frequencies that had been active prior to the mixing process in the form of a constructive interference among individual spin-packets. Also as in the z-case above, this spatial helix of spin-packets can be wound and unwound numerous times by periodically reversing the $Y_{l,m}$ acquisition gradient, in a process that will encode the spin frequencies as a function of $t_2$ and thereby enable the collection of 2D NMR spectra within a single scan. The actual shapes of the resulting k-echoes—shapes which will in turn define the kind of peaks observed in ultrafast experiments along the indirect domain—will depend on the sample's and gradient's spatial dependencies. The echo positions on the other hand will be independent of these details, and solely reflect a site's given $\Omega_1$ shift. As can be appreciated from this Figure numerical simulations reveal a behavior that overall is uniform, with minor line shape differences that can be rationalized in terms of the characteristics assumed for the gradients and the sample.

Figure 11:
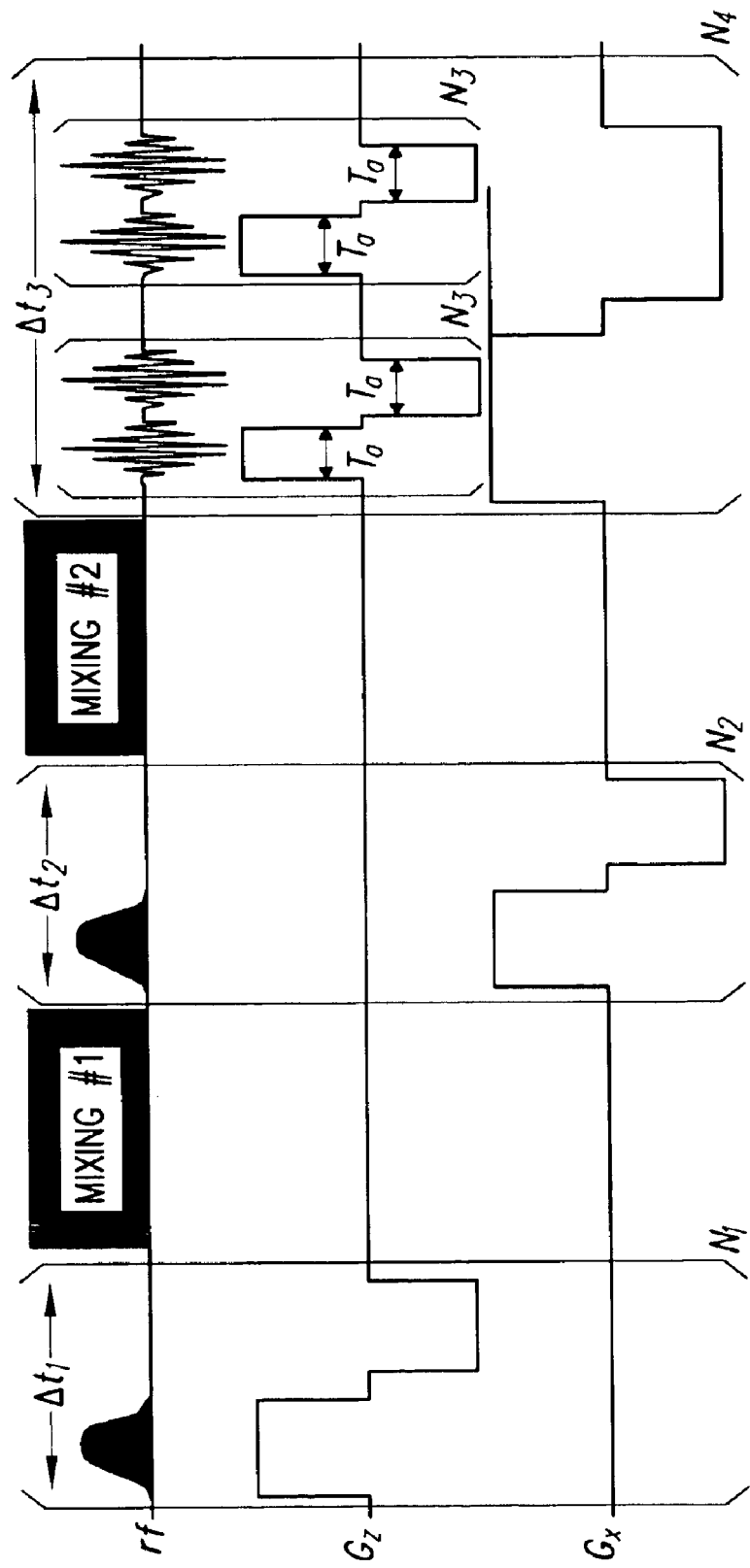
FIG. 11 illustrates conceptually the invention as shown in FIG. 1 regarding the application of the invention concerning the ultrafast acquisition of 3D NMR spectra.

It follows from these considerations that only if identical gradient geometries are employed to impose the initial spatial encoding and the subsequent decoding of the internal frequencies, will a successful unraveling of the indirect evolution frequencies result. By contrast, the application of an intermediate gradient that is orthogonal to the one employed in the initial excitation, will neither add nor detract from the unwinding demands placed on the acquisition gradient. This in turn opens up a route for extending the protocol introduced in the preceding paragraphs to include the encoding of an additional indirect dimension, if modified as illustrated in FIG. 11. FIG. 11 shows a basic scheme proposed for the single-scan collection of 3D NMR spectra. A train of frequency-shifted pulses is first applied to achieve the spatial encoding of spins throughout different axial positions in the sample ($t_1$); this is followed by a second rf-driven encoding of the spin evolution during $t_2$ along a linearly independent radial direction. Data are finally collected while in the presence of oscillating acquisition gradients, which decode the initial $\Omega_1$, $\Omega_2$ frequencies along the ($k_z, k_x$) axes while monitoring the spin evolution along a third ($t_3$) time axis. The actual direction (or even linearity) of the gradients used in the encoding is not fundamental.

Such scheme incorporates two separate gradients arranged along linearly independent geometries, which implement two consecutive spatial encodings of the spin evolution. Each one of these encoding processes, assumed here for simplicity to lie along the x and z directions, proceeds independently and along an outline similar to the one described previously for the single-axis 2D NMR method or experiment. The first of these gradients will thus induce an $\Omega_1 t_1$-dependent winding of the spin-packets along the z direction, while for each one of these z slices the second gradient will generate an $\Omega_2 t_2$-dependent encoding along the x axis. Because of the ensuing "double-winding" of spin-packets the overall bulk magnetization is again reduced to zero, and an acquisition process implemented on the resulting sample will be associated with a null initial signal. Moreover, by contrast to the 2D encoding case, no single-axis gradient would be able by itself of regenerating an observable signal from such an initial state. Only the simultaneous application of $G_z$, $G_x$ acquisition gradients can succeed in aligning the spin-packets, wound as they now are along two orthogonal encoding directions. In order to find the conditions leading to such an alignment the inventive method implements again a step or protocol where both x and z gradients are rapidly and independently oscillated. The digitized signal can then be regarded as a function of three independent variables: $k_z \propto \int G_z(t)dt$; $k_x \propto \int G_x(t)dt$; and a time $t_3$ associated with the final free evolution frequency $\Omega_3$. When the k-wave numbers happen to fulfill the $k_z = -C_z \Omega_1$ and $k_x = -C_x \Omega_2$ conditions, spin-packets throughout the sample will interfere constructively and result in an observable echo. FT of this sharp 2D echo signal along the remaining $t_3$ dimension provides then a means or way for characterizing all ($\Omega_1$, $\Omega_2$, $\Omega_3$) evolution frequencies experienced by the spins throughout the course of the method or experiment, from data collected within a single scan. Since the mechanisms by which peaks are originated in this kind of 3D NMR experiments are identical to the ones that were earlier described for ultrafast 2D NMR acquisitions, most of the arguments used to derive Nyquist and line shape criteria along the indirect dimension of the latter can be directly extrapolated to the indirect dimensions of the former.

Figure 12A:
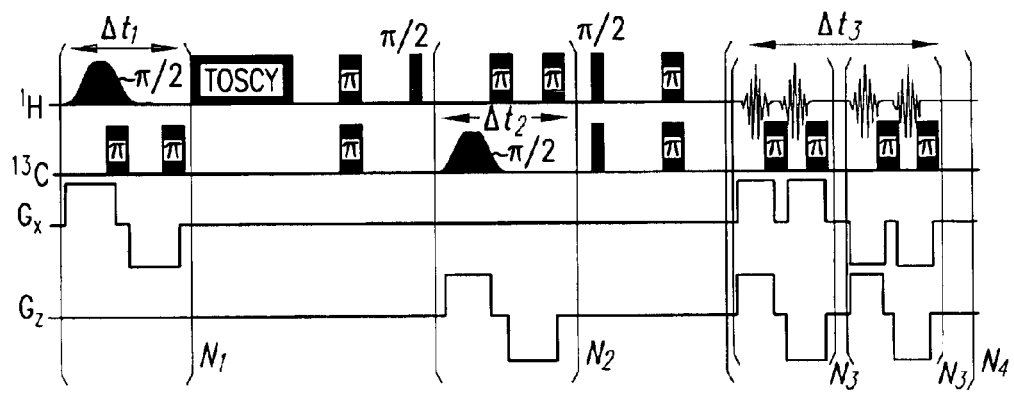
FIGS. 12A–D demonstrate the inventive method illustrated in FIG. 11, with the single-scan acquisition (≈140 ms) of a 3D NMR spectrum on glycerol/$D_2O$.
Figure 12B:
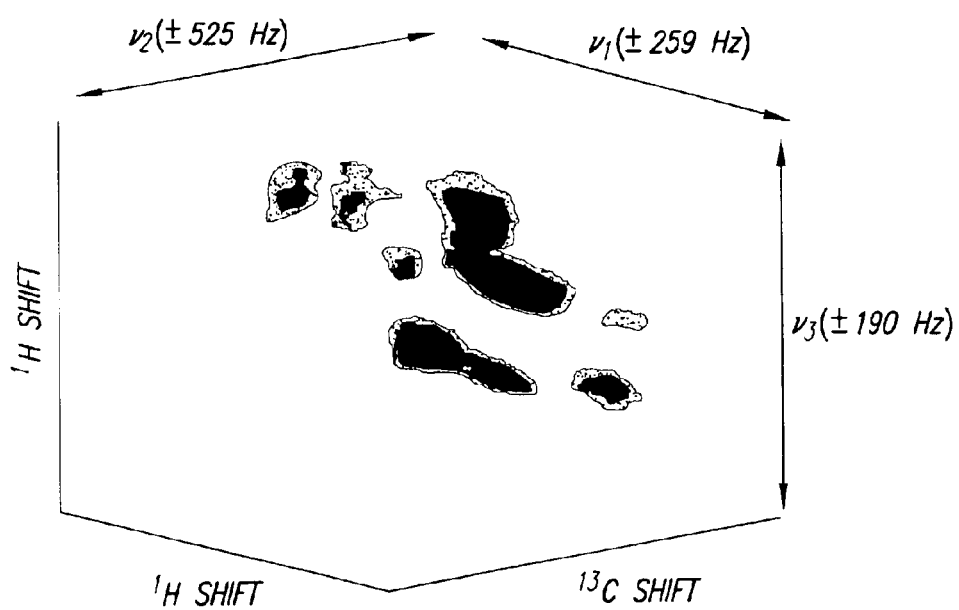
Figure 12C:
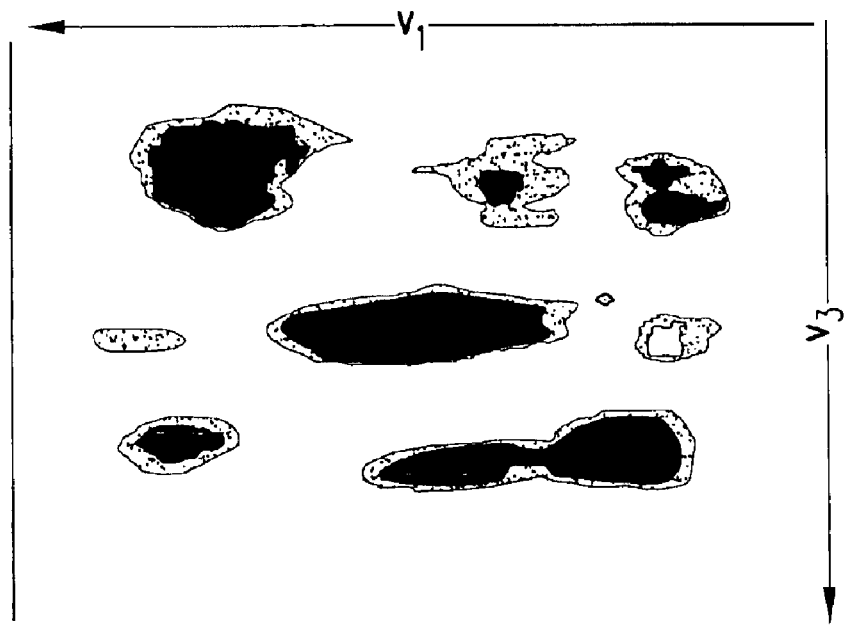
Figure 12D:
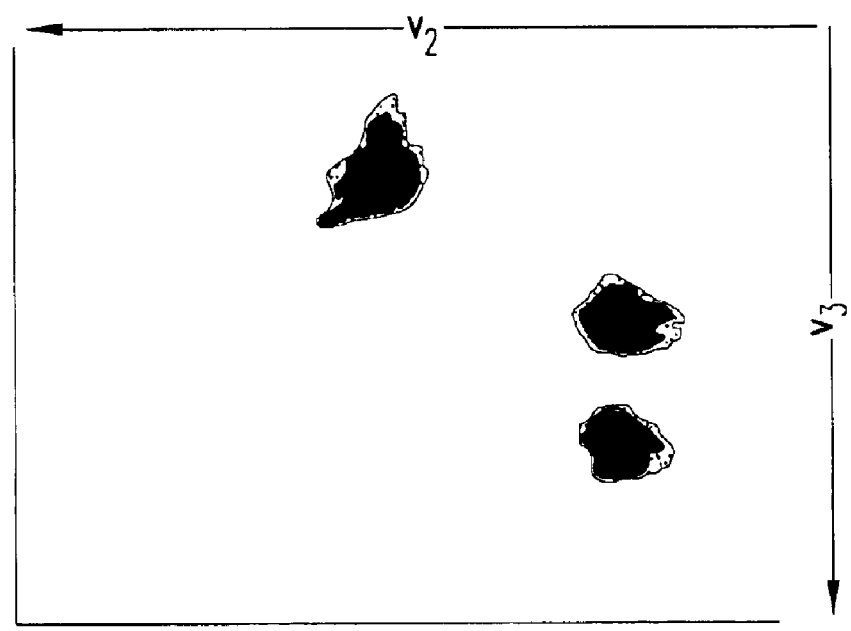

FIGS. 12A to 12D demonstrate the inventive method illustrated and described with reference to FIG. 11. FIG. 12A shows a TOCSY-HSQC pulse sequence assayed to corroborate the possibility of collecting a 3D NMR spectrum within a single scan. FIG. 12B depicts an iso-surface representation of the full 3D NMR spectrum acquired on a glycerol/$D_2O$ sample, using the pulse sequence indicated in FIG. 12A. The total time required to carry out this experiment was ca. 141 ms. FIGS. 12C and 12D illustrate 2D contours resulting from projecting the 3D NMR data against the remaining spectral axis, and illustrate the expected line shapes for the compound. Excitation parameters included $N_1$=11, $N_2$=17, all selective pulses 256-$\mu$s-long Gaussians applied at 4 kHz offset increments, a 160 kHz/cm z gradient, and a 100 kHz/cm x gradient. Initial and final heteronuclear transfer periods were set at 1.75 and 1.40 ms respectively. Acquisition parameters included $N_3$=6, $N_4$=24, $T_a$=60 $\mu$s, 1.5 $\mu$s physical dwell times, maximum x and z gradient strengths of 88 kHz/cm and 9 kHz/cm respectively. Such conditions yielded 88×6×24 points in the mixed ($v_2/k_z$, $v_1/k_x$, $t_3$) domain, which were processed as into a 128×16×64-point magnitude spectrum.

FIGS. 12A to 12D gives experimental proof on the feasibility of implementing single-scan 3D NMR, utilizing a $^1$H-$^{13}$C-$^1$H TOCSY-HSQC experiment on a glycerol/$D_2O$ sample, see as example J. Cavanagh, W. J. Fairbrother, A. G. Palmer III and N. J. Skelton, "Protein NMR Spectroscopy: Principles and Practice" Academic Press, San Diego, 1996. This heteronuclear correlation relies on the coherent nature of heteronuclear S→I transfer, which will preserve the spatial encoding imparted by a train of RF pulses even while the nature of the nuclei that carry such encoding changes, in order to parallelize the manner by which the heteronuclear evolution is encoded. FIG. 12A illustrates a pulse sequence based on such premise; FIG. 12B shows the experimental results obtained with such sequence.

Having discussed how the principles of single-scan 2D NMR can be extended to a third dimension and having illustrated the method for accomplishing this objective, the method of the invention can be adapted and can be extended to an arbitrary number of dimensions. The principles underlying the invention, as explained in detail above, can be generalized to an arbitrary number of dimensions. Such generalization is made possible by the countless gradient geometries that can, in principle, be utilized for encoding the spin evolution, represented for instance by the spherical harmonic set $\{Y_{l,m}\}$ discussed earlier. When applied in combination with a train of frequency selective RF pulses, any of these eigen functions can be employed to wind an independent spiral of spin-packets, of the type summarized by the Fourier relation in eq. (9). The task of unraveling the spin evolution frequencies that act along various indirect dimensions becomes then equivalent to scanning simultaneously the multiple $k_{l,m}$ axes associated to these various gradients. Such a procedure can in principle always be carried out within a single continuous acquisition, provided that flexible enough gradients are available.

Figure 13A:
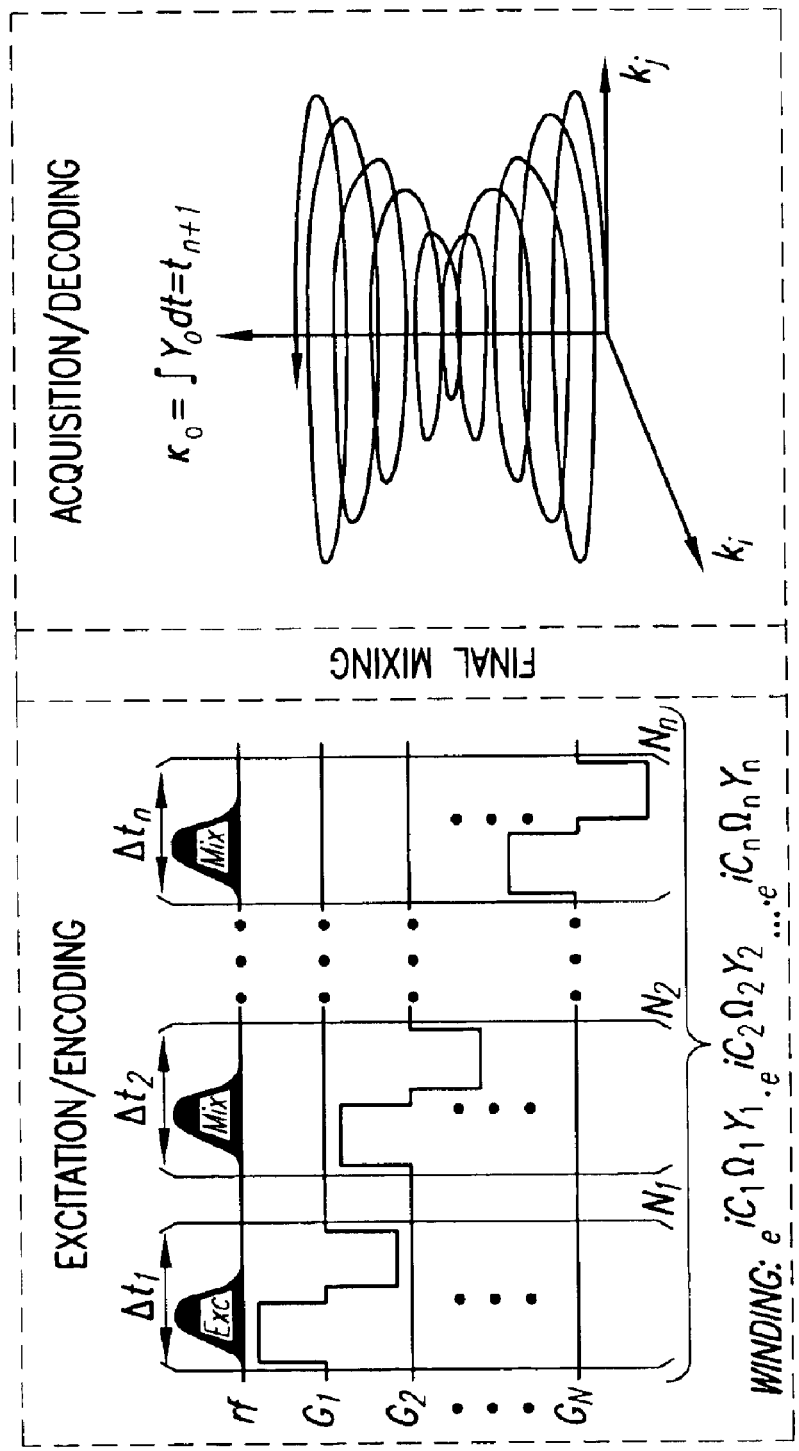
FIGS. 13A–B shows the present invention as applied to the acquisition of arbitrary N-dimensional NMR spectra (A), and illustrates that according to the invention a single-scan 4D NMR experiment can be completed within 94 ms (B).
Figure 13B:
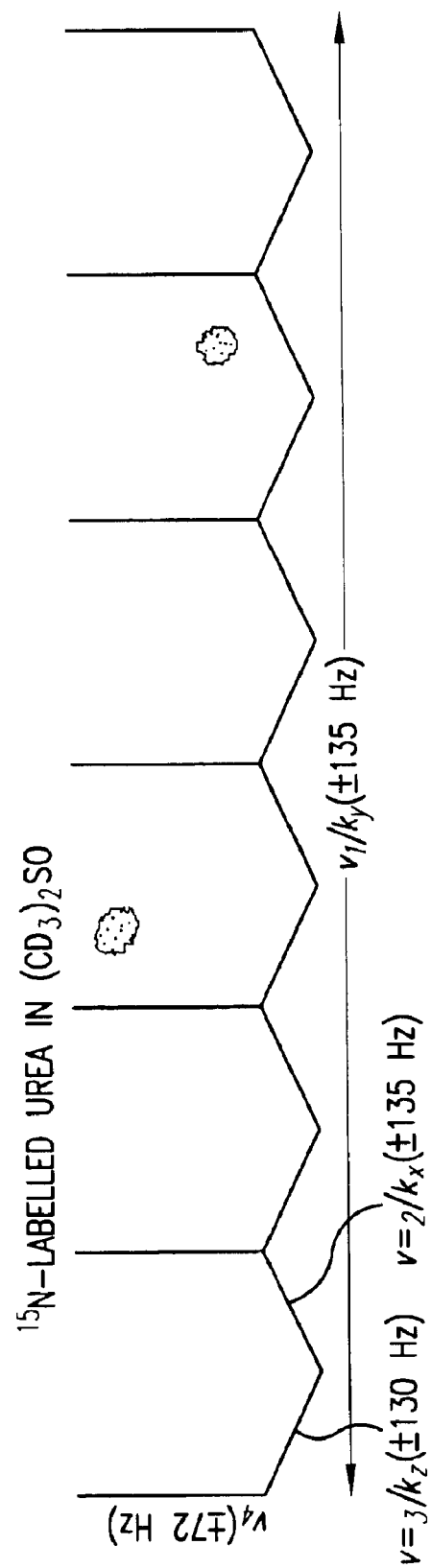

FIGS. 13A and 13B show the present invention applied to the acquisition of arbitrary N-dimensional NMR spectra. In FIG. 13A the method step is shown, of the present invention, for the acquisition of arbitrary N-dimensional NMR spectra, and involving N−1 independent spatial encoding events prior to the last mixing event, and their simultaneous decoding during the course of the signal acquisition. FIGS. 13A and 13B Illustrate the method of the present invention with respect to the acquisition of a 4D NMR technique or experiment within a single scan, that can be completed within 94 ms. As no actual mixing sequence is here involved between any of the $t_i$ $t_{i+1}$ intervals, the two peaks of this compound show as expected along the main diagonal of the 4D spectral space (grayscale isosurfaces). Excitation parameters included 19 pulses applied along x and y axes (500 $\mu$s long), and 25 pulses along the z direction (250 $\mu$s long). The acquisition yielded 6×6×12×6 points in the mixed ($v_1/k_y$, $v_2/k_x$, $v_3/k_z$, $t_4$) domain, which were processed into the displayed 6×16×32×16 point magnitude spectrum.

The portrayal in FIGS. 13A and 13B summarizes the kind of method or scheme that would then be involved in these arbitrary N-dimensional experiments; the graph in FIG. 13B illustrates experimental 4D NMR results collected on the practice of the disclosed method on the basis of such principles, with the triple-axes spatial encoding required by such sequence implemented with the aid of x, y, z spectroscopy gradients applied in combination with a constant-time protocol. Collecting similar spectra using conventional means might have taken several hours, perhaps even days, of continuous spectrometer use.

The present invention also provides a new method to significantly shorten the times needed to collect unidimensional NMR spectra recorded from so-called heteronuclear spins X—basically any NMR targets of investigation other than protons. 1D NMR studies on $^{15}$N and $^{13}$C nuclei in particular, have a great potential for chemical structure determination and play irreplaceable roles in both modern industry and academia. Because of the greatly reduced magetogyric ratios $\gamma$ characterizing these nuclei in comparison to $^1$H, however, the signal arising from $^{15}$N and $^{13}$C after a standard NMR experiment is usually less sensitive than its $^1$H counterpart by a factor of $(\gamma_H/\gamma_X)^2$: a factor $\gamma_H/\gamma_X$ reflecting the smaller magnetic fields that the heteronucleus X can generate, and another $\gamma_H/\gamma_X$ factor consequence of the higher Larmor frequency in which for a given field strength the $^1$H NMR acquisition takes place. During the development of 2D NMR as a tool for biomolecular investigations, it was realized that this penalty in signal-to-noise could be compensated if heteronuclear experiments were carried out in "inverse detection" mode; i.e., if the heteronuclear evolution were encoded along the indirect domain of a 2D experiment, and these information then passed over to a neighboring $^1$H on which the actual measurement would take place. This mode of operation, however, finds limited application toward the acquisition of 1D $^{15}$N and $^{13}$C NMR data due to the fact that the organic or pharmaceutical chemist is usually not interested in paying the orders-of-magnitude longer acquisition times that are inherent to 2D over 1D forms of spectroscopy. The invention hereby presented, however, can easily overcome this time limitation. The starting point for doing so is again the pulse sequence illustrated in FIG. 1, but modified so as to "suspend" the information encoded along the direct domain. This essentially requires collapsing the direct-domain $^1$H NMR spectral information using a train of composite refocusing $\tau$ pulses. This collapsing of the 2D NMR information into a single heteronuclear dimension should enable gaining considerable factor in sensitivity when compared with an analogous 1D heteronuclear acquisition. When considering that for a given signal-to-noise ratio NMR acquisition times decrease as the square of an experiment's sensitivity, the potential savings that might result from implementing these sensitivity-enhanced 1D modes of acquisition become evident.

Figure 14A:
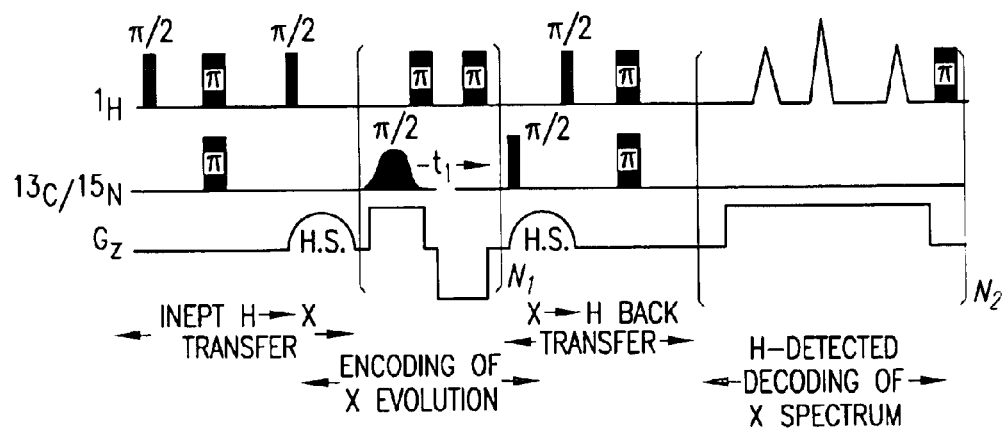
FIGS. 14A–C demonstrate the potential of the invention to increase the sensitivity of unidimensional NMR acquisitions on heteronuclei (i.e., nuclei other than protons) by relying on spatially-selective indirect-detection protocols.
Figure 14B:
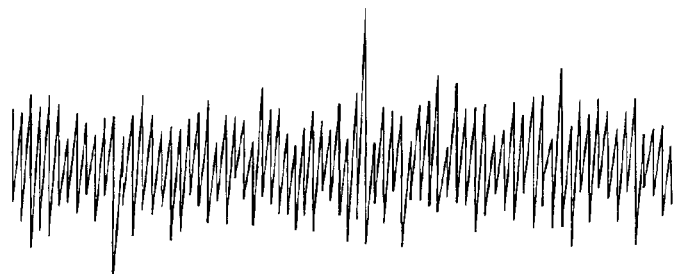
Figure 14C:
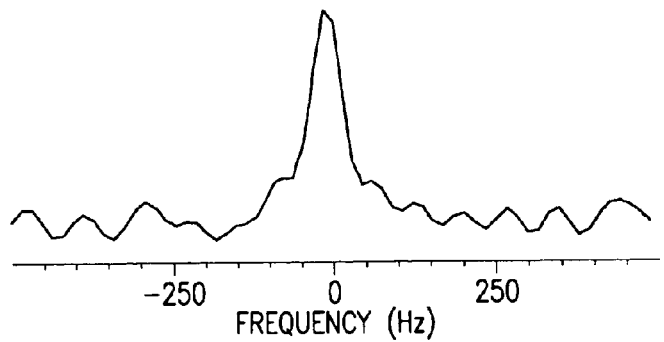

FIG. 14 demonstrates the feasibility of achieving significant signal-to-noise improvements in this manner, using 1D NMR of the $^{15}N$ nuclei as example. The sequence assayed for this test (FIG. 14A) consisted of an initial INEPT block whereby $^1H$ z magnetization ($H_z$) was coherently transformed into two-spin $H_zN_z$ spin order; a frequency selective train of $^{15}N$ radiofrequency pulses which in combination with the invention hereby proposed encodes the spin evolution of nitrogen spins along the sample's spatial orientation; a second INEPT-like period where this nitrogen encoding is transferred back to protons via a two-spin order state; and a final acquisition period combining a mono-polar decoding gradient with a train of $^1H$ τ pulses that effectively freezes the $^1H$ information and allows for the acquisition of a large number of identical $^{15}N$ spectra within a single scan. All these spectra are then co-added for the sake of additional improvements in signal-to-noise. The indirectly-detected NMR spectrum of a 25 mM $^{15}N$ urea sample dissolved in $d_6$-DMSO was collected in this manner, and compared with the standard direct acquisition usually used in 1D NMR. Whereas in a single scan an experiment based on direct monitoring of the $^{15}N$ spins the NMR signal is barely discernible from the background noise (FIG. 14B), an indirectly-detected 1D single-scan experiment leads to the presence of an unambiguous signal (FIG. 14C and much higher signal-to-noise ratios.

Figure 15A:
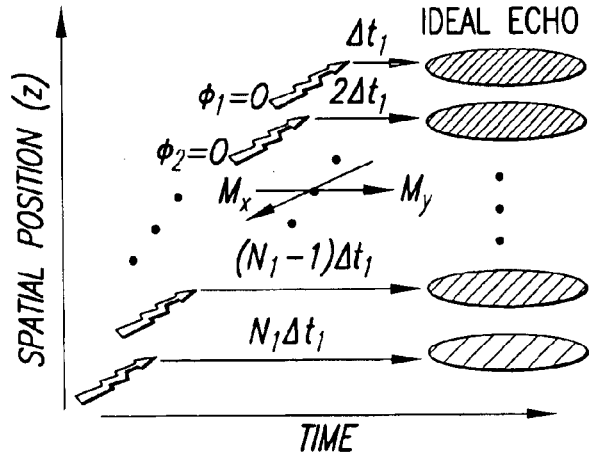
FIGS. 15A–C give a schematic description of how the invention could be used to retrieve high resolution NMR spectra even when dealing with inhomogeneous magnetic field, by manipulating the phases of the RF pulses used in the slice selection for implementing a compensation in the field strengths experienced by spins in inequivalent slices.
Figure 15B:
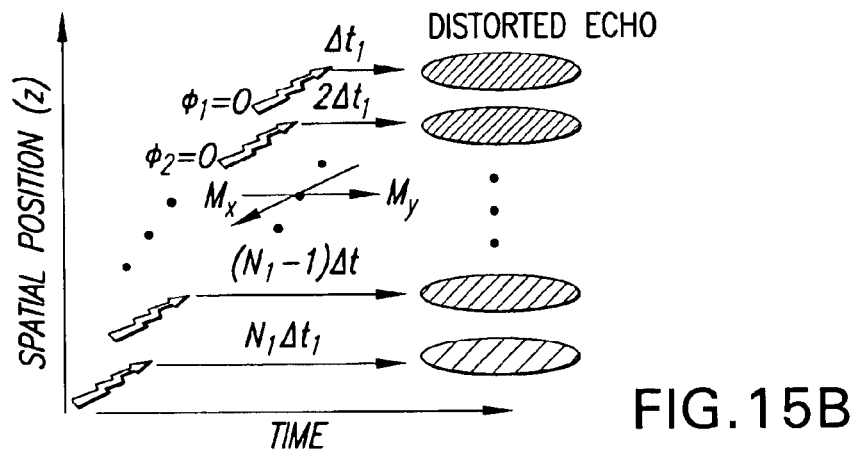
Figure 15C:
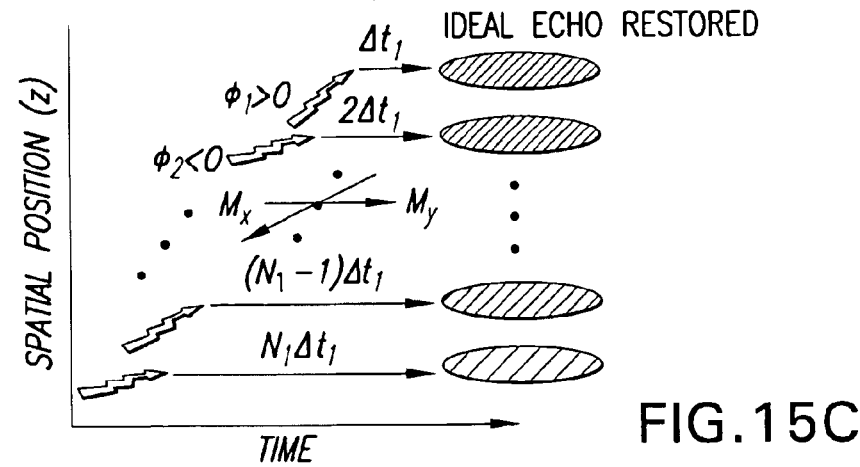

The present invention also provides a method for acquiring high resolution NMR spectra showing narrow resonance line widths, even in the presence of large static inhomogeneities or dynamic fluctuations in the main magnetic field. Achieving highly uniform, constant magnetic fields, with inhomogeneities of up to a few parts-pre-billion (ppb) throughout the sample volume and drift rates of the same order of magnitude over the duration of an experiment, is one of the most important and challenging demands posed to developers of NMR and MRI instrumentation. Magnetic field inhomogeneities or instabilities larger than this size preclude the retrieval of chemical shift spectral information, and complicate the achievement of high spatial imaging resolution. A large fraction of the cost of magnetic resonance instrumentation is thus commonly invested in achieving these extremely uniform magnetic fields, employing advanced wiring materials and highly complex designs that include the addition of a considerable number of sophisticated "shimming" magnetic field gradients onto the main magnetic field. In every instance this shimming procedure is costly and time consuming. Moreover important occasions arise when shimming to ppb homogeneity is simply unattainable, for instance when dealing with MRI investigations on tissues with a high degree of anisotropic magnetic susceptibility or with "inside-out" setups of the kind used when employing NMR for water logging and oil prospecting (G. Coates, *NMR logging: Principles and Applications*, 1999). By opening an alternative to the usual acquisition of NMR spectra by directly detecting the spins' time-domain signal, the new invention hereby discussed provides a route for compensating for these artificial inhomogeneities. To explain how this compensation would operate we treat first the case of static inhomogeneities, which endowes spins at different positions in the sample with artificially different Larmor precession frequencies. The starting point for the compensation scheme lies then in encoding the evolution frequencies of subdivided spin-packets according to their spatial position using the principles illustrated in FIGS. 1–4. We assume now that in addition to the natural spin evolution frequencies of interest there will be an encoding stemming from the undesired field inhomogeneities, which of course will not be at all as significant within the individual slices as it is on the much larger sample as a whole. Still, precession frequencies will adopt different values when considered from slice to slice due to the latter's inequivalent positions and—just as they do in conventionally-detected time-domain NMR—affect the sharply-defined echo peaks that would otherwise be recorded (FIGS. 15A, 15B). On the other hand these inhomogeneities are static and thus their value can be precisely measured, for instance by mapping the spatial distribution of the main static magnetic field upon first installing it. Once the dependence of the magnetic field inhomogeneity ΔB with position $z_j$ is accurately known, a compensation for its effects can be easily introduced into the scheme of FIG. 1 by manipulating the phases of the RF pulses involved in the spatial selection as illustrated in FIG. 15C. Phase corrections $\phi_j \approx -\Delta B(z_j)[Cz_j+T_a]$ are here introduce, which compensate for the effects of static distortions over the sample as a whole but leave the effects of the internal evolution frequencies unchanged. These can thus be measured as detailed in FIGS. 3 and 4 of the present application. The main factor limiting how large a field inhomogeneity can be accounted for in this manner becomes the relative size of the field gradient $G_e$ used to impart the spatially-selective excitation, as this defines the "fine-ness" of the spatial selection and in turn the inhomogeneity within the slice. Preliminary calculations indicate that for conventional 1D inhomogeneity profiles field dispersions in the order of 100s ppm can be accounted for in this manner, and provide high-resolution NMR spectra in the presence of magnetic field dispersions that are orders of magnitude larger than those which can be nowadays be tolerated. Furthermore, the extension of a unidimensional scheme like the one illustrated in FIG. 15C to a three-dimensional case based on the concurrent utilization of x-y-z orthogonal field gradient sets, is straightforward.

In addition of enabling for the compensation of static, pre-mapped inhomogeneities, the scheme described in the preceding paragraph could be used to compensate for dynamic magnetic field instabilities, and thereby enable the acquisition of 2D NMR spectra in such rapidly-drifting magnetic systems. This is a field of emerging importance, as the highest fields currently available for performing magnetic resonance measurements are generated by hybrid superconducting/Bitter designs relying on high-current direct-current (DC) power supplies. Due to the impossibility to regulate such intense current supplies down to parts-per-billion perfection the magnetic fields that they generate drift—usually by several ppm/sec. Such drift rates are incompatible with the acquisition of high-resolution NMR spectra in general, and with 2D NMR spectroscopy in particular. The invention hereby presented will help alleviate these problems on the basis of two accounts: i) by shortening the overall times needed for completing a multidimensional NMR experiment by several orders of magnitude, instabilities occurring over a >1 sec time scale cease to be a concern, and ii) by opening up the possibility to compensate for field instabilities by manipulating the RF excitation phases in the manner put forward in FIG. 15C, short term instabilities (<1 sec) can also be taken care of. The first of these features follows clearly from the detailed description give above. To deal with the second of these features, the noise-like instabilities arising from DC power supplies, we propose carrying out the phase corrections detailed in the previous paragraph but in a real-time manner. This is conceptually analogous to correcting a pre-mapped field fluctuation, with the exception that the phases $\phi(z_j)$ involved in the field compensation would have to be computed at the time of an RF pulse application. This in turn would need a circuit for monitoring the instantaneous changes in magnetic field occurring since the beginning of the NMR acquisition, something which can be implemented utilizing an ancillary electronic circuitry akin to the one normally incorporated in the deuterium lock circuits of high-resolution NMR instruments (see for instance E. Fukushima & W. Roeder, "*Experimental Pulsed NMR: A Nuts and Bolts Approach*" Addison, 1981). Multidimensional NMR studies in unregulated hybrid or electromagnets, could thus become a reality.

The present invention also contemplates a method for the analysis or monitoring by multidimensional NMR of rapidly changing dynamic systems. As it is possible by the present invention to complete the collection of multidimensional NMR spectra within a 0.1 sec time scale, the method of the present invention can enable monitoring in real time, a variety of chemical and physical processes and reactions that are hitherto outside the capabilities of NMR. These include the real-time monitoring of ongoing chemical reactions, and the folding of biological macromolecules, as described in C. M. Dobson and P. J. Hore, *Nat. Struct. Biol.* 5, 504 (1998). According to the present invention this is accomplished by a method for the real-time monitoring of a chemical or physical process comprising the steps of: (1) conducting a chemical or physical processin real-time; (2) monitoring the on-going chemical or physical process in real time by repeatedly acquiring multidimensional nuclear magnetic resonance spectra within a single scan at preselected short time intervals; each single scan being carried out comprising the steps of the methods described herein previously in detail. For example, the single scan can be carded out by: (3) partitioning a predetermined sample of the on-going chemical or physical process into a set of independent subensembles; (4) applying the single scan to the sample by exciting the set of subensembles by a time-incremented series of selective excitation sequences; (5) generating a signal from each subensemble; (6) homogenously mixing the generated signals; and (7) simultaneously acquiring a complete multidimensional nuclear magnetic resonance data set for each preselected short time interval.

The application of multidimensional NMR to hyperpolarized spin states is described by B. M. Goodson, J. Magn. Reson. 155, 157 (2002) and P. J. Carson, C. R. Bowers, D. P. Weitekamp J. Am. Chem. Soc. 123, 11821 (2001). A number of methods have been developed to enable the generation of very highly polarized spin states. These systems can impart on atoms and molecules NMR signals that are ca. five orders of magnitude more intense than a conventional NMR signal, but they are transient states that decay relatively rapidly and take long times to be generated. Only single-scan experiments are thus usually implemented on such hyperpolarized spin systems. The present invention can enable the routine application of complex multidimensional NMR experiments to such hyperpolarized systems, enabling extensions of chemical studies as described by B. S. Duckett, S. A. Colebrooke, *Encyclopedia of Nuclear Magnetic Resonance*, 9, 598 (2002), and of clinical studies as described by M. S. Albert, C. D. Cates, B. Driehuys, W. Happer, B. Saam, C. S. Springer Jr., A. Wishnia, Nature, 370, 199 (1994). This is carried out by the present invention by the method of for the real-time monitoring of a hyperpolarized spin system comprising the steps of: (1) monitoring an on-going hyperpolarized spin system in real time by repeatedly acquiring multidimensional nuclear magnetic resonance spectra within a single scan at preselected short time intervals; each single scan being carried out comprising the steps of the methods described herein previously in detail. For example, the single scan can be carried out by: (2) partitioning a predetermined sample of the on-going hyperpolarized spin system into a set of independent subensembles; (4) applying the single scan to the sample by exciting the set of subensembles by a time-incremented series of selective excitation sequences; (5) generating a signal from each subensemble; (6) homogenously mixing the generated signals; and (7) simultaneously acquiring a complete multidimensional nuclear magnetic resonance data set for each preselected short time interval.

The present invention has particular application to the characterization of analytes subject to flow through a NMR spectrometer, and thereby the coupling of multidimensional NMR with high-throughput chromatographic techniques. As described in H. H. Liu, C. Felten, Q. F. Xue, B. L. Zhang, P. Jedrzejewski, B. Karger, M. E. Lacey, R. Subramanian, D. L. Olson, A. G. Webb and J. V. Sweedler, *Chem. Rev.* 99, 3133 (1999) and K. Albert, *On-Line Liquid Chromatography-NMR and Related Techniques*. (John Wiley & Sons Ltd., Chichester, 2002), the combination of NMR with chromatographic techniques would be one of the most promising routes to the characterization of chemical and biochemical samples, if it were possible to do so. The residence time of such flowing samples through the NMR reception coil, however, is very limited ($\approx$1 sec). Therefore only unidimensional NMR spectra have been so far collected in real time on these kinds of samples. By the method of the present invention acquisition of multidimensional NMR spectra on samples being chromatographed can be accomplished, thereby providing a new and much more powerful way to characterize plant extracts, natural products, amino acids, peptides, nucleic acids and other types of chemicals being separated in a chromatographic column. This is accomplished by the present invention by the method for the real-time monitoring of one or more samples of a material undergoing a chromatographic technique comprising the steps of: (1) monitoring an on-going chromatographic technique in real time by repeatedly acquiring multidimensional nuclear magnetic resonance spectra within a single scan at preselected short time intervals; each single scan being carried out comprising the steps of the methods described herein previously in detail. For example, the single scan can be carried out by: (2) partitioning a predetermined sample of the on-going chromatographic technique into a set of independent subensembles; (3) applying the single scan to the sample by exciting the set of subensembles by a time-incremented series of selective excitation sequences; (4) generating a signal from each subensemble; (5) homogenously mixing the generated signals; and (6) simultaneously acquiring a complete multidimensional nuclear magnetic resonance data set for each preselected short time interval.

The rapid survey of large numbers of chemicals like those made nowadays available by Combinatorial Chemistry. As explained in K. C. Nicolau, R. Hanko, W. Hartwig, *Handbook of Combinatorial Chemistry: Drugs, Catalysts, Materials*. (Wiley-VCH Verlag, Weinheim, 2002), Combinatorial Chemistry is a novel approach to the synthesis of organic, inorganic and pharmacological molecules, whereby thousands of compounds are synthesized and tested in a variety of ways for chemical and/or biological activity. Combinatorial methods have provided much of the impetus for the ongoing revolution currently undergoing in Proteomics and Metabonomics. The enormous number of compounds that this approach requires be tested only allows high-throughput analytical techniques to participate in these tests and characterizations. The invention described in this patent will now allow the incorporation of ultrafast multidimensional NMR methods to this array of high-throughput techniques, thereby providing a new route to the discovery of new catalysts, new pharmaceuticals, pharmaceutically-active peptides and nucleic acids, etc. This is accomplished by the present invention by the method for the rapid and real-time monitoring of a combinatory chemistry involving a plurality of samples of a number of different materials comprising the steps of: (1) rapidly monitoring an on-going combinatorial chemistry technique involving a plurality of samples in real time by repeatedly successively acquiring multidimensional nuclear magnetic resonance spectra within a single scan of successive samples; each single scan being carried out with respect to a sample and comprising the steps of the methods described herein previously in detail. For example, the single scan can be carried out by: (2) partitioning each successive sample of the ongoing combinatorial chemistry technique into a set of independent subensembles; (3) applying the single scan to the sample by exciting the set of subensembles by a time-incremented series of selective excitation sequences; (4) generating a signal from each subensemble; (5) homogenously mixing the generated signals; and (6) simultaneously acquiring a complete multidimensional nuclear magnetic resonance data set for each successive sample.

The acceleration of quantum computing algorithms is described by D. G. Cory, A. F. Fahmy, T. F. Havel, Proc. Natl. Acad. Sci. USA, 94, 1634 (1997). NMR offers one of the most practical approaches to implement a quantum computer. A variety of such algorithms has been proposed and demonstrated based on multidimensional NMR, as described in Z. L. Madi, R. Bruschweiler, R. R. Ernst, *J. Chem. Phys.* 109, 10603 (1998). The present invention enables the speeding up of such multidimensional NMR quantum computers by several orders of magnitude. This is accomplished by the present invention by the method for controlling a multidimensional NMR quantum computer with respect to a sample of a material comprising the steps of: (1) rapidly monitoring a multidimensional NMR quantum computer with respect to a sample in real time by acquiring multidimensional nuclear magnetic resonance spectra within a single scan of the sample, and using the spectra for controlling the operation of the multidimensional NMR quantum computer. The single scan is carried out with respect to the sample and comprises the steps of the methods described herein previously in detail. For example, the single scan can be carried out by: (2) partitioning the sample into a set of independent subensembles; (3) applying the single scan to the sample by exciting the set of subensembles by a time-incremrented series of selective excitation sequences; (4) generating a signal from each subensemble; (5) homogenously mixing the generated signals; and (6) simultaneously acquiring a complete multidimensional nuclear magnetic resonance data set for the respective sample.

Structural elucidations of large molecules, and in particular of systems involving proteins and nucleic acids are described in V. Tugarinov, et al., *J. Am. Chem. Soc.* 124, 10025 (2002). NMR-based structural elucidations on high molecular weight, complex systems will eventually demand the use of a large number of spectral dimensions (over 4) for achieving sufficient spectral resolution of the peaks. At the same time, however, large molecules in general and biological macromolecules under physiological conditions in particular, are usually incapable of withstanding the long acquisition times hitherto associated with such experiments. By speeding the times required to implement such experiments by several orders of magnitude, the present invention bypasses such limitation, providing a new way to obtain the structure of macromolecules in their native states. This is accomplished present invention by the method for the structural elucidations of a large molecule with respect to a sample of a molecule comprising the steps of: (1) rapidly monitoring a large molecule with respect to a sample in real time by acquiring multidimensional nuclear magnetic resonance spectra within a single scan of the sample, and using the spectra for elucidating the large molecule. It may be necessary to repeat the single scan a multiple of times to obtain a set of spectra. The single scan is carried out with respect to the sample and comprises the steps of the methods described herein previously in detail. For example, the single scan can be carried out by: (2) partitioning the sample into a set of independent subensembles; (3) applying the single scan to the sample by exciting the set of subensembles by a time-incremented series of selective excitation sequences; (4) generating a signal from each subensemble; (5) homogenously mixing the generated signals; and (6) simultaneously acquiring a complete multidimensional nuclear magnetic resonance data set for the respective sample.

A further subordinate method of the present invention concerns ultrafast multidimensional NMR that can be applied regarding in vivo spectroscopy and the following of fast metabolic processes, as described in M. S. Cohen, Ed., *Physiological NMR Spectroscopy: From Isolated Cells to Man*, Ann. N. Y. Acad. Sci. (vol. 508, New York, 1987), both in basic research as well as in clinical diagnosis applications, such as described in M. A. Thomas, et al., *Magn. Reson. Med.* 46, 58 (2001). Indeed multidimensional NMR spectroscopy on animals and/or humans is currently hampered by the long times that subjects need to reside within the NMR magnet for the completion of the experiments, a demand which should be greatly eased by the practice of this novel invention. This will enable a new route to the clinical diagnosis of disease as described by E. T. Fossel, *Diagnosis of cancer by NMR spectroscopy of blood lipoproteins and triglycerides*. U.S. Pat. No. 4,918,021 (1990), 18 pp. and by M. A. Brown and R. C. Semelka, *MRI: Basic Principles and Applications*, Wiley-Liss, New York, 1999, whether as a pure spectroscopic tool or in combination with methods for spatial localization. This is accomplished by present invention by the method for in vivo spectroscopy with respect to a sample comprising the steps of: (1) rapidly monitoring the sample in real time by acquiring multidimensional nuclear magnetic resonance spectra within a single scan of the sample, and using the spectra for evaluating the sample. It may be necessary to repeat the single scan a multiple of times to obtain a set of spectra. The single scan is carried out with respect to the sample and comprises the steps of the methods described herein previously in detail. For example, the single scan can be carried out by: (2) partitioning the sample into a set of independent subensembles; (3) applying the single scan to the sample by exciting the set of subensembles by a time-incremented series of selective excitation sequences; (4) generating a signal from each subensemble; (5) homogenously mixing the generated signals; and (6) simultaneously acquiring a complete multidimensional nuclear magnetic resonance data set for the respective sample.

Due to the reliance of the invention on magnetic field gradients, further subordinate methods concern ultrafast NMR making it also amenable to incorporate a variety of MRI protocols. This opens new routes for the accelerated acquisition of clinical diagnostic and research MR images, along the lines described in F. Schmitt, M. K. Stehling, R. Turner, *Echo Planar Imaging: Principles, Technique, Application* (Berlin, Springer, 1998). The new ultrafast multidimensional MRI invention that results can be employed to monitor brain metabolism, pulsating regions (thorax, abdomen), etc. It can also aid for the real-time positioning of malignancies and hence as aid in surgical procedures. This is accomplished by present invention by the method for magnetic resonance imaging with respect to a sample comprising the steps of: (1) rapidly monitoring the sample in real time by acquiring multidimensional nuclear magnetic resonance spectra within a single scan of the sample at a preselected short time interval during the performance of an MRI protocol, and using the spectra for evaluating the sample or creating an image of the sample. It may be necessary to repeat the single scan a multiple of times to obtain a set of spectra and to obtain a plurality of images. The single scan is carried out with respect to the sample and comprises the steps of the methods described herein previously in detail. For example, the single scan can be carried out by: (2) partitioning the sample into a set of independent subensembles; (3) applying the single scan to the sample by exciting the set of subensembles by a time-incremented series of selective excitation sequences; (4) generating a signal from each subensemble; (5) homogenously mixing the generated signals; and (6) simultaneously acquiring a complete multidimensional nuclear magnetic resonance data set for the respective sample.

The extension of single-scan multidimensional spectroscopy can be applied to techniques other than NMR. Over the last decade, the concepts underlying multidimensional NMR have also been extended and demonstrated in other types of spectroscopies: mass spectrometry (A. G. Marshall, F. R. Verdun, *Fourier Transforms in NMR, Optical, and Mass Spectrometry: A User's Handbook* (Elsevier, Amsterdam, 1990)), electron paramagnetic resonance (A. Schweiger, G. Jeschke, *Principles of Pulsed Electron Paramagnetic Resonance* (Oxford University Press, Oxford, 2001)), as well as a variety of pulsed infrared, optical and UV spectroscopies (S. Mukamel, *Ann. Rev. Phys. Chem* 51, 691 (2000)). As in the case of NMR these techniques have based on monitoring the response of the system as a function of an incremented time variable, thereby requiring the collection and processing of numerous individual scans. By adapting the ideas of a reversible inhomogeneous frequency broadening coupled to the selective excitation of sub-ensembles within the sample, the present invention can enable non-MNR multidimensional spectroscopy to be reduced to a single-scan acquisition. This is accomplished by present invention by the method for non-MNR multidimensional spectroscopy with respect to a system comprising the steps of: (1) rapidly monitoring the system in real time by acquiring spectra based on the response of the system as a function of an incremented time variable within a single scan of the system at a preselected short time interval during the functioning of the system, and using the spectra for evaluating the system or creating an image of the system. It may be necessary to repeat the single scan a multiple of times to obtain a set of spectra and to obtain a plurality of images. The single scan is carried out with respect to the system and comprises the steps of the methods described herein previously in detail. For example, the single scan can be carried out by: (2) partitioning the system or its region of interest into a set of independent subensembles; (3) applying the single scan to the system or ROI by exciting the set of subensembles by a time-incremented series of selective excitation sequences; (4) generating a signal from each subensemble; (5) homogenously mixing the generated signals; and (6) simultaneously acquiring a complete multidimensional data set for the system.

Figure 16:
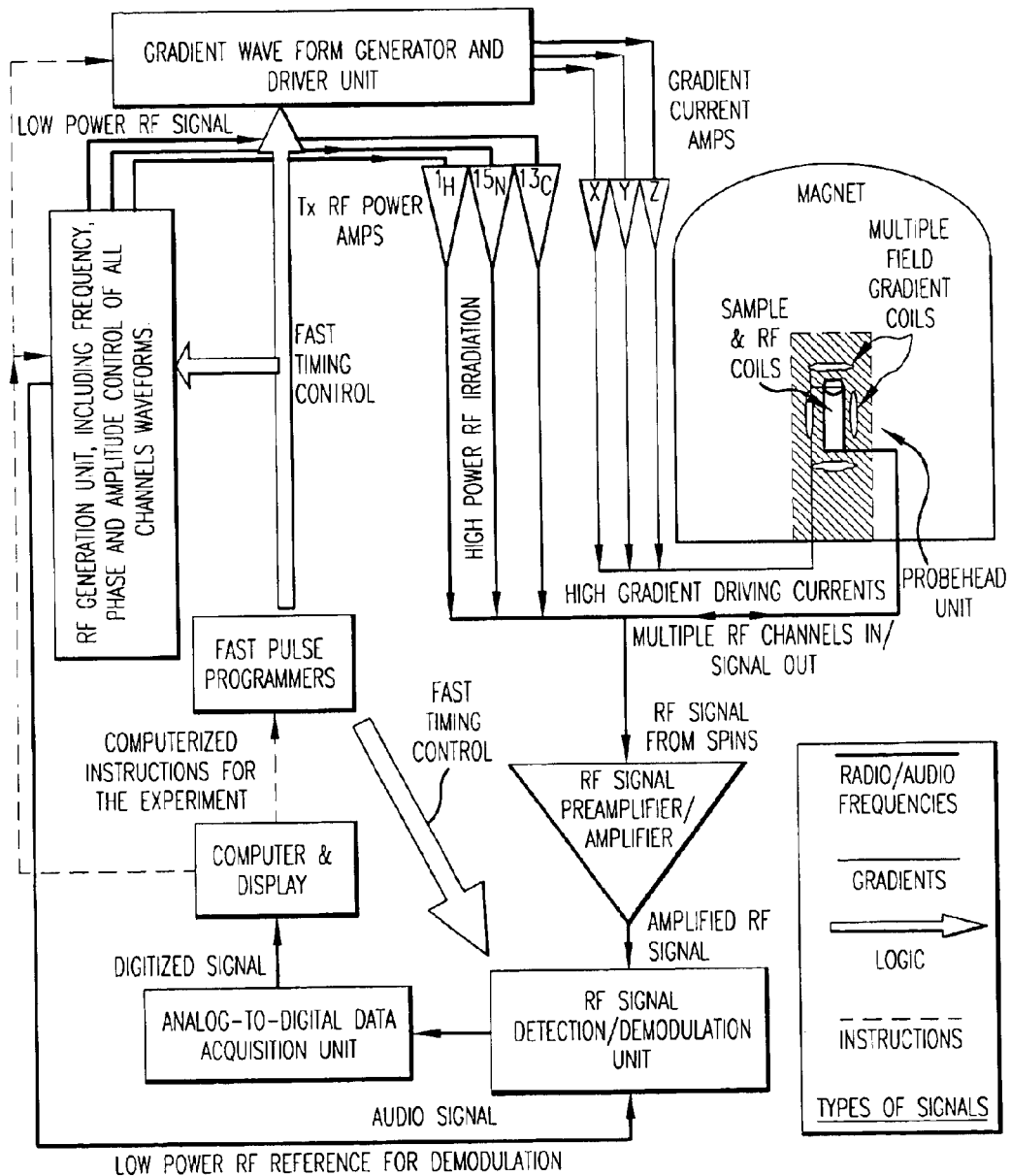
FIG. 16 is a block diagram of a preferred embodiment of the apparatus of the present invention with respect to NMR/MRI.

Referring now to FIG. 16, there is shown in block diagram a preferred embodiment of an NMR/MRI apparatus according to the present invention with the types of signals shown in the block diagram shown in the legend box at the lower right of the drawing. As shown, the apparatus consists of a magnet 100 that generates a high-quality, high-intensity magnetic field that is uniform within the volume of a sample 106 undergoing test or monitoring. As shown, the magnet is made of a superconducting wire, and includes an ancillary shim coil system for achieving a part-per-million homogeneity over the desired volume. Included within this embodiment are the coils 102 for generating the magnetic field gradients required by the invention. The magnetic field strength is normally stabilized with the aid of an additional locking circuitry. Within a probehead unit 104 in the magnet 100 is positioned the sample 106 and RF coils 108.

The probehead unit 104 ("probe") contains the sample 106 to be studied, as well as ancillary electronic equipment, including the coils 102 needed for generating the field gradients required by the invention, the electronics associated with an efficient RF irradiation of the spins, and the circuitry for an efficient detection of the spins' signal. Numerous such gradient and RF circuits are present in the single probe; the former for accounting for the three spatial directions, the latter for the simultaneous irradiation of multiple nuclear species ($^1H$, $^2H$, $^{13}C$, etc.).

The gradient wave form generator and driver unit 110 is comprised of a digital gradient waveform generator and a gradient driver that translates these digital signals into low-level analog currents, which are fed to gradient amplifiers X, Y, Z via lines 140 where these low-level signals are translated into intense high gradient driving currents that are supplied via lines 142 to the gradient coils 102 surrounding the sample 106. Three such units are independently present, driving orthogonal x, y and z geometries.

RF Generation and Irradiation Unit 112 is comprised of an RF unit having a low-level synthesizer generating the basic low power RF signal used to irradiate a spin, an amplitude- and phase-control stage capable of creating pulses of different frequencies and shapes. Unit 112 is coupled via lines 136 to and feeds high-power amplifiers 114 that translate these low-level signals into the intense pulses that are fed via lines 138 to common lines 139 into the RF coils 108 in the probe 104 for the actual irradiation. Common lines 139 serve as multiple RF Channels In/Signals Out. Unit 112 also provides a reference RF for the subsequent demodulation of the spins' signal from the radio (MHz) to the audio (kHz) range via line 134 to RF Signal Detection/Demodulation Unit 124. Several such units are usually present, one per spin species to be irradiated during a particular sequence ($^1H$, $^3C$, $^{15}N$, $^2H$, etc.).

A Signal Detection Unit receives the RF signal from spins via multiple RF channels In/Signals Out line 139 and coupled line 144. The Unit is comprised of an RF signal preamplifier/amplifier 120 to effect the requisite preamplification, and then, amplification. Preamplifier/amplifier 120 is coupled, in turn, to an RF Signal Detection/Demodulation unit 124 including the functions of demodulation and detection, which in turn is coupled to an Analogto-Digital Data Acquisition Unit 126 that contains the digitization components, capable of transforming the voltage originally generated by the spins following their irradiation into a string of complex numbers (the Free Induction Decay or FID).

A Computer and Display 130 is coupled to Fast Pulse Programmers 132, which receive instructions from the computer 130, via bus 150, as indicated in FIG. 13. These components 130 and 132 are responsible for interfacing to the user, and then creating the desired sequence of commands that all remaining units in the apparatus will carry out during the course of the operation of the apparatus or the experiment. Thus, the computer 130 also provides instructions via bus 152 to the RF generation unit 112 and to the Gradient Wave Form Generator Driver Unit 110. In accordance with standard computer practice, users commands, input via a standard I/O 154, such as a keyboard or other such input device, are translated by the computer 130 into strings of binary digits and logical timing signals, that are in turn executed by the various units. The computer 130 containing adequate memory is also usually the final depository of the digitized FID, where its data is processed into an NMR spectrum according to the algorithms and other information set forth above and display takes place. The Fast Pulse Programmers 132 are connected by buses 160 and 162 to provide fast timing control to the RF Signal Detection/Demodulation Unit 124, the RF generation unit 112 and the Gradient Wave Form Generator and Driver Unit 110.

Figure 17:
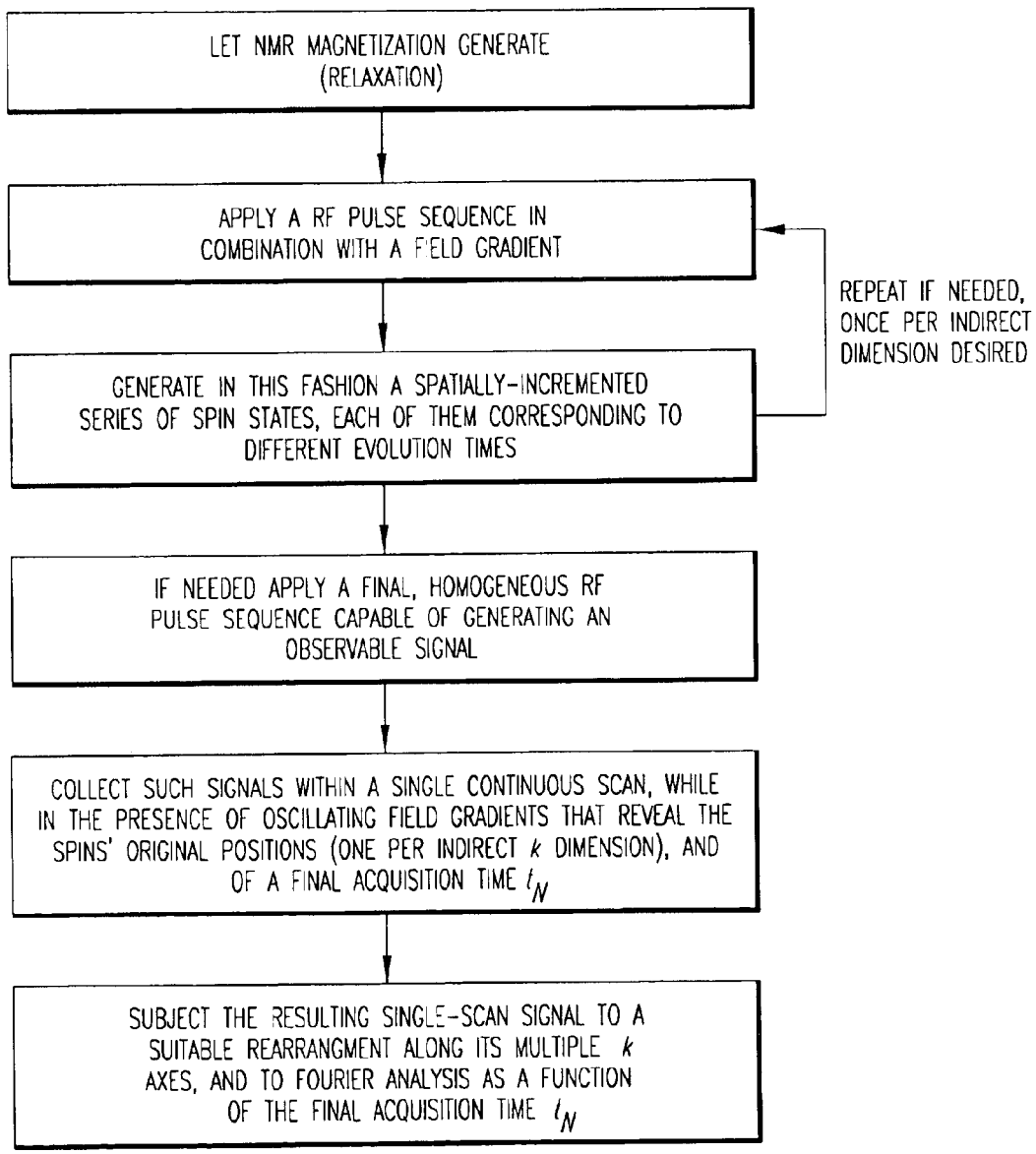
FIG. 17 is a flow chart illustrating the inventive method as it is applied towards the acquisition of multidimensional NMR spectra.

Referring now to the flow chart of FIG. 17, the invention will now be explained as it applies to the acquisition of multidimensional NMR spectra. After, a sample 106 has been placed in the probehead 104 within the magnet 100 in proper juxtaposition to the gradient coils 102 and the RF coils 108, the first step Si is to let NMR magnetization generate to obtain relaxation. In step S2, an RF pulse sequence derived from RF generation unit 112 is applied to the sample 106 in combination with a field gradient obtained from the Gradient Wave Form Generator and Driver Unit 110. In step S3 in this fashion a spatially-incremented series of spin states is generated in sample 106, each spin state corresponding to different evolution times. This step S3 can be repeated, if needed, once per indirect dimension as desired, as indicated by the loop back shown in the flow chart from step S3 to step S2. Then in step S4, if needed, a final homogenous RF pulse sequence is applied capable of generating an observable signal.

In step S5 the signals are collected within a single continuous scan, while in the presence of oscillating field gradients that reveal the spins original positions (one per indirect k dimension), and of a final acquisition time $t_N$. Finally, in step S6, the resulting single-scan signal is subjected to a suitable rearrangement along its multiple k axes, and to Fourier analysis as a function of the final acquisition time $t_N$.

The present invention (i.e., system or apparatus described in detail in this description of specific embodiments and as generally depicted in FIG. 16 or any part thereof) may be implemented using hardware, software or a combination thereof and may be implemented in one or more computer systems or other processing systems, and the capability would be within the skill of one ordinarily skilled in the art of programming of computers from the teachings and detailed disclosure provided in the foregoing description of the apparatus and the process. The computer system of the invention represents any single or multi-processor computer, and in conjunction therewith, single-threaded land multi-threaded applications can be used. Unified or distributed memory systems can be used. In one example, the system and method of the present invention is implemented in a multi-platform (platform independent) programming language such as Java, programming language/structured query language (PL/SQL), hyper-text mark-up language (HTML), practical extraction report language (PERL), Flash programming language, common gateway interface/structured query language (CGI/SQL) or the like and can be implemented in any programming language and browser, developed now or in the future, as would be apparent to a person skilled in the relevant art(s) given this description. In another example, the system and method of the present invention, may be implemented using a high-level programming language (e.g., C++) and applications written for the Microsoft Windows NT or SUN OS environments. It will be apparent to persons skilled in the relevant art(s) how to implement the invention in alternative embodiments from the teachings herein.

The Computer system of the invention includes one or more processors and can execute software implementing the routines described above, such as shown in FIG. 17. Various software embodiments are described in terms of this exemplary computer system. After reading this description, it will become apparent to a person skilled in the relevant art how to implement the invention using other computer systems and/or computer architectures.

The Computer system can include a display interface that forwards graphics, text and other data from the communication infrastructure (or from a frame buffer not shown) for display on the display unit included as part of the system.

The Computer system also includes a main memory, preferably random access memory (RAM), and can also include a secondary memory. The secondary memory can include, for example, a hard disk drive and/or a removable storage drive, representing a floppy disk drive, a magnetic tape drive, an optical disk drive, etc. The removable storage drive can read from and/or write to a removable storage unit in a well-known manner.

In alternative embodiments, a secondary memory may include other similar means for allowing computer programs or other instructions to be loaded into computer system. Such means can include, for example, a removable storage unit and an interface. Examples can include a program cartridge and cartridge interface (such as that found in video game console devices), a removable memory chip (such as an EPROM, or PROM) and associated socket, and other removable storage units and interfaces that allow software and data to be transferred from the removable storage unit to computer system.

The Computer system can also include a communications interface that allows software and data to be transferred between computer system and external devices via a communications path. Examples of communications interface can include a modem, a network interface (such as Ethernet card), a communications port, interfaces described above, etc. Software and data transferred via a communications interface are in the form of signals that can be electronic, electromagnetic, optical or other signals capable of being received by communications interface, via a communications path. Note that a communications interface provides a means by which computer system can interface to a network such as the Internet.

The present invention can be implemented using software running (that is, executing) in an environment similar to that described above with respect to FIG. 14. In this document, the term "computer program product" is used to generally refer to removable storage unit, a hard disk installed in hard disk drive, or a carrier wave carrying software over a communication path (wireless link or cable) to a communication interface. A computer useable medium can include magnetic media, optical media, or other recordable media, or media that transmits a carrier wave or other signal. These computer program products are means for providing'software to the computer system.

Computer programs (also called computer control logic) are stored in main memory and/or secondary memory. Computer programs can also be received via a communications interface. Such computer programs, when executed, enable the computer system to perform the features of the present invention as discussed herein. In particular, the computer programs, when executed, enable the processor to perform features of the present invention. Accordingly, such computer programs represent controllers of the computer system.

The present invention can be implemented as control logic in software, firmware, hardware or any combination thereof. In an embodiment where the invention is implemented using software, the software may be stored in a computer program product and loaded into computer system using a removable storage drive, hard disk drive, or interface. Alternatively, the computer program product may be downloaded to computer system over a communications path. The control logic (software), when executed by the one or more processors, causes the processor(s) to perform functions of the invention as described herein.

In another embodiment, the invention is implemented primarily in firmware and/or hardware using, for example, hardware components such as application specific integrated circuits (ASICs). Implementation of a hardware state machine so as to perform the functions described herein will be apparent to persons skilled in the relevant art(s) from the teachings herein.

Although the present invention has been described in terms of specific preferred embodiments, nevertheless modifications and changes will become apparent to those of skill in the art from the teachings herein. Such modifications and changes as will be readily apparent to those skilled in the art are deemed to fall within the purview of the invention as set forth in the claims appended hereto.

What is claimed is:

1. A method for treating a sample to acquire multidimensional spectra within a single scan comprising the steps of: (1) partitioning a sample into a set of independent subensembles endowed with different resonance frequencies; (2) implementing a polychromatic irradiation of the sample whereby the various subensembles are selectively manipulated by a time-incremented series of excitation or refocusing sequences; (3) generating an observable spectral signal from each of the subensembles; (4) simultaneously monitoring the observable signals arising from the set of subensembles in a resolved fashion; (5) processing the observable signals acquired in this manner into a complete multidimensional spectral data set.

2. The method for treating a sample according to claim 1 wherein step (3) includes applying to the subensembles a homogeneous sequence.

3. The method of claim 1 wherein the partitioning effected during the excitation and acquisition periods is effected notionally.

4. The method of claim 1 wherein the polychromatic irradiation and the resolved fashion is selected to suit the particular kind of spectroscopy associated with the spectral data set.

5. The method of claim 4 wherein the spectroscopy includes one of optical, paramagnetic electron, mass and nuclear magnetic resonance (NMR) origin.

6. The method of claim 1 wherein the scan is completed in 1 second.

7. The method of claim 1 wherein the scan is completed in about 0.1 seconds.

8. The method of claim 1 wherein the homogenous sequence is in the form of a pulse.

9. The method of claim 1 wherein the homogenous sequence is in the form of a series of impulses.

10. The method of claim 1 in which magnetic field gradients are used for excitation, refocusing, and resolved acquisition.

11. The method of claim 1 wherein a spatial encoding of the resonance frequencies is effected.

12. The method of claim 1 wherein the single scan is repeated a preselected number of times to obtain a plurality of complete multidimensional spectral data sets.

13. A method for treating a sample to acquire multidimensional magnetic resonance spectra within a single scan comprising the steps of: (1) applying a magnetic field gradient on the sample so as to endow spins at different positions within the sample with different resonance frequencies; (2) applying a train of frequency-selective radiofrequency (RF) pulses in unison with this gradient so as to endow spins at different positions within the sample with incremented values of their evolution times, thus creating an effective spatial encoding of the spins' frequencies (3) creating a set of observable spin signals; (4) capturing the signals thus created from the sample while decoding the spins' spatial locations using a second set of acquisition magnetic field gradient; (5) subjecting the collected data to a suitable rearrangement and Fourier analysis procedure so as to retrieve the final spectrum being sought.

14. The method of claim 13 wherein the magnetic field gradient oscillates.

15. The method of claim 13 wherein steps (1) to (4) are repeated a small number of times.

16. The method of claim 13 wherein step (3) includes applying a homogeneous mixing pulse sequence at the conclusion of the spatial encoding.

17. The method of claim 13 wherein the scan is completed in 1 second.

18. The method of claim 13 wherein the scan is completed in about 0.1 seconds.

19. The method of claim 13 wherein step (1) is carried out using multiple linearly-independent gradient geometries.

20. The method of claim 13 wherein step (5) includes digitizing of the collected data prior to Fourier analysis.

21. The method of claim 13 wherein step (2) is carried out using a single 90 degree excitation followed by a train of spatially selective 180 degree refocusing pulses.

22. The method of claim 13 wherein step (2) is carried out using a single chirp excitation pulse.

23. The method of claim 13 wherein step (2) is carried out by a first train of frequency-selective radiofrequency (RF)- pulses to create a first spatial encoding along one direction followed by a second train of frequency-selective radiofrequency (RF) pulses to create additional spatial encodings along different direction.

24. The method of claim 13 wherein step (2) is carried out by a first train of frequency-selective radiofrequency (RF) pulses to create a first spatial encoding along one direction followed by a second train of frequency-selective radiofrequency (RF) pulses to create additional spatial encodings along a different geometry.

25. The method of claim 13 wherein step (2) is carried out by a first train of frequency-selective radiofrequency (RF) pulses to create a first spatial encoding along one direction followed by a second train of frequency-selective radiofrequency (RF) pulses to create additional spatial encodings along a different direction and geometry.

26. The method of claim 13 wherein step (2) is carried out by a first train of frequency-selective radiofrequency (RF) pulses to create a first spatial encoding along one direction followed by additional trains of frequency-incremented radiofrequency (RF) pulses to create additional spatial encodings along different directions.

27. The method of claim 13 wherein step (2) is carried out by a first train of frequency-selective radiofrequency (RF) pulses to create a first spatial encoding along one direction followed by additional trains of frequency-selective radiofrequency (RF) pulses to create additional spatial encodings along different geometries.

28. The method of claim 13 wherein step (2) is carried out by a first train of frequency-selective radiofrequency (RF) pulses to create a first spatial encoding along one direction followed by additional trains of frequency-selective radiofrequency (RF) pulses to create additional spatial encodings along different directions and geometries.

29. The method of claim 13 wherein multiple distinctive spatial encodings are created.

30. The method of claim 13 wherein spatially localized MRI information is retrieved in combination with multidimensional NMR spectra by means of further numerical manipulations on the single scan (or few scans) data.

31. Apparatus for treating a sample to acquire multidimensional spectra within a single scan comprising (1) means for partitioning a sample into a set of independent subensembles endowed with different resonance frequencies; (2) means for implementing a polychromatic irradiation of the sample whereby the various subensembles are selectively manipulated by a time-incremented series of excitation or refocusing sequences; (3) means for generating an observable spectral signal from each of the subensembles; (4) means for simultaneously monitoring the observable signals arising from the set of subensembles in a resolved fashion; and (5) means for processing the observable signals acquired in this manner into a complete multidimensional spectral data set.

32. The apparatus for treating a sample according to claim 31 wherein the means for generating an observable spectral signal includes means for applying to the subensembles a homogeneous sequence.

33. The apparatus of claim 31 wherein the partitioning effected during the excitation and acquisition periods is effected notionally.

34. The apparatus of claim 31 wherein the polychromatic irradiation and the resolved fashion is selected to suit the particular kind of spectroscopy associated with the spectral data set.

35. The apparatus of claim 34 wherein the spectroscopy, includes one of optical, paramagnetic electron, mass and nuclear magnetic resonance (NMR) origin.

36. The apparatus of claim 31 wherein the scan is completed in 1 second.

37. The apparatus of claim 31 wherein the scan is completed in about 0.1 seconds.

38. The apparatus of claim 31 wherein the homogenous sequence is in the form of a pulse.

39. The apparatus of claim 31 wherein the homogenous sequence is in the form of a series of impulses.

40. The apparatus of claim 31 in which magnetic field gradients are used for excitation, refocusing, and resolved acquisition.

41. The apparatus of claim 31 wherein a spatial encoding of the resonance frequencies is effected.

42. The apparatus of claim 31 wherein the single scan is repeated a preselected number of times to obtain a plurality of complete multidimensional spectral data sets.

43. Apparatus for treating a sample to acquire multidimensional magnetic resonance spectra within a single scan comprising (1) means for applying a magnetic field gradient on the sample so as to endow spins at different positions within the sample with different resonance frequencies; (2) means for applying a train of frequency-selective radiofrequency (RF) pulses in unison with this gradient so as to endow spins at different positions within the sample with incremented values of their evolution times, thus creating an effective spatial encoding of the spins' frequencies (3) means for creating a set of observable spin signals; (4) means for capturing the signals, thus created from the sample while decoding the spins' spatial locations using a second set of acquisition magnetic field gradient; and (5) means for subjecting the collected data to a suitable rearrangement and Fourier analysis procedure so as to retrieve the final spectrum being sought.

44. Apparatus of claim 43 wherein the magnetic field gradient oscillates.

45. Apparatus of claim 43 further including means for repeating the scan a small number of times.

46. Apparatus of claim 43 including means for applying a homogeneous mixing pulse sequence at the conclusion of the spatial encoding.

47. Apparatus of claim 43 wherein the scan is completed in 1 second.

48. Apparatus of claim 43 wherein the scan is completed in about 0.1 seconds.

49. Apparatus of claim 43 wherein means are provided for using multiple linearly-independent gradient geometries.

50. Apparatus of claim 43 wherein means are provided for digitizing of the collected data prior to Fourier analysis.

51. Apparatus of claim 43 wherein said means for applying a train of frequency-selective radiofrequency (RF) pulses is carried out using a single 90 degree excitation followed by a train of spatially selective 180 degree refocusing pulses.

52. Apparatus of claim 43 wherein the means for applying a train of frequency-selective radiofrequency (RF) pulses is carried out using a single chirp excitation pulse.

53. Apparatus of claim 43 wherein the means for applying a train of frequency-selective radiofrequency (RF) pulses is carried out by a first train of frequency-selective radiofrequency (RF) pulses to create a first spatial encoding along one direction followed by a second train of frequency-selective radiofrequency (RF) pulses to create additional spatial encodings along different direction.

54. Apparatus of claim 43 wherein the means for applying a train of frequency-selective radiofrequency (RF) pulses is carried out by a first train of frequency-selective radiofrequency (RF) pulses to create a first spatial encoding along one direction followed by a second train of frequency-selective radiofrequency (RF) pulses to create additional spatial encodings along a different geometry.

55. Apparatus of claim 43 wherein the means for applying a train of frequency-selective radiofrequency (RF) pulses is carried out by a first train of frequency-selective radiofrequency (RF) pulses to create a first spatial encoding along one direction followed by a second train of frequency-selective radiofrequency (RF) pulses to create additional spatial encodings along a different direction and geometry.

56. Apparatus of claim 43 wherein the means for applying a train of frequency-selective radiofrequency (RF) pulses) is carried out by a first train of frequency-selective radiofrequency (RF) pulses to create a first spatial encoding along one direction followed by additional trains of frequency-incremented radiofrequency (RF) pulses to create additional spatial encodings along different directions.

57. Apparatus of claim 43 wherein the means for applying a train of frequency-selective radiofrequency (RF) pulses is carried out by a first train of frequency-selective radiofrequency (RF) pulses to create a first spatial encoding along one direction followed by additional trains of frequency-selective radiofrequency (RF) pulses to create additional spatial encodings along different geometries.

58. Apparatus of claim 43 wherein the means for applying a train of frequency-selective radiofrequency (RF) pulses is carried out by a first train of frequency-selective radiofrequency (RF) pulses to create a first spatial encoding along one direction followed by additional trains of frequency-selective radiofrequency (RF) pulses to create additional spatial encodings along different directions and geometries.

59. Apparatus of claim 43 wherein multiple distinctive spatial encodings are created.

60. Apparatus of claim 43 wherein spatially-localized MRI information is retrieved in combination with multidimensional NMR spectra by means of further numerical manipulations on the single scan (or few scans) data.

* * * * *